(12) United States Patent
Tanaka et al.

(10) Patent No.: US 8,778,613 B2
(45) Date of Patent: Jul. 15, 2014

(54) AFFINITY RESIN

(75) Inventors: Akito Tanaka, Kisarazu (JP); Takaaki Shiyama, Osaka (JP); Akira Yamazaki, Suita (JP)

(73) Assignee: Reverse Proteomics Research Institute Co., Ltd., Kisarazu-Shi (JP)

( * ) Notice: Subject to any disclaimer, the term of this patent is extended or adjusted under 35 U.S.C. 154(b) by 1724 days.

(21) Appl. No.: 10/573,165

(22) PCT Filed: Oct. 15, 2004

(86) PCT No.: PCT/JP2004/015659
§ 371 (c)(1),
(2), (4) Date: Nov. 22, 2006

(87) PCT Pub. No.: WO2005/037881
PCT Pub. Date: Apr. 28, 2005

(65) Prior Publication Data
US 2007/0167594 A1    Jul. 19, 2007

(30) Foreign Application Priority Data

Oct. 17, 2003 (JP) .................................. 2003-357144
Jun. 16, 2004 (JP) .................................. 2004-178808

(51) Int. Cl.
| | |
|---|---|
| *G01N 33/53* | (2006.01) |
| *G01N 33/545* | (2006.01) |
| *G01N 33/543* | (2006.01) |
| *C08F 220/36* | (2006.01) |
| *A61K 6/083* | (2006.01) |
| *C08L 33/10* | (2006.01) |
| *B01J 20/26* | (2006.01) |

(52) U.S. Cl.
CPC .............. *G01N 33/53* (2013.01); *G01N 33/543* (2013.01); *G01N 33/545* (2013.01); *C08F 220/36* (2013.01); *A61K 6/083* (2013.01); *C08L 33/10* (2013.01); *B01J 20/267* (2013.01)
USPC ............ 435/7.1; 435/7.92; 436/531; 436/541

(58) Field of Classification Search
CPC ... G01N 33/53; G01N 33/543; G01N 33/545; C08F 220/36; A61K 6/083; C08L 33/10; B01J 20/267
See application file for complete search history.

(56) References Cited

U.S. PATENT DOCUMENTS

| | | | | |
|---|---|---|---|---|
| 5,073,611 | A | * | 12/1991 | Rehmer et al. ................. 526/208 |
| 6,515,039 | B1 | | 2/2003 | Ulbricht et al. |
| 2006/0177943 | A1 | | 8/2006 | Tanaka et al. |

FOREIGN PATENT DOCUMENTS

| | | |
|---|---|---|
| EP | 1553412 A1 | 7/2005 |
| JP | 63-105014 A | 5/1988 |
| JP | 05-023395 A | 2/1993 |
| JP | 05-311194 A | 11/1993 |
| JP | 06-256434 A | 9/1994 |
| JP | 2003-231648 A | 8/2003 |
| WO | WO 9711067 A1 * | 3/1997 |
| WO | WO 00/12575 A1 | 3/2000 |
| WO | WO 2004/025297 A1 | 3/2003 |

OTHER PUBLICATIONS

Song et al. Preparation of UV-curable emulsions using PEG-modified urethane acrylates: the effect of nonionic and anionic groups. Journal of Applied Polymer Science, 1996, vol. 62, pp. 1775-1782.*
Cook et al. Polymerization kinetics of oligo (ethylene oxide) and oligo (methylene) oxide dimethacrylates. Journal of Polymer Sciences 1993, vol. 31, pp. 1063-1067.*
Song et al. Preparation of UV-curable emulsions using PEG-modified urethane acrylates: the effect of nonionic and anionic groups. Journal of Applied Polymer Sciences,1996, vol. 62, pp. 1775-1782.*
Shiyama et al., "Design and synthesis of novel hydrophilic spacers for the reduction of nonspecific binding proteins on affinity resins," *Bioorganic & Medicinal Chemistry*, 12(11):2831-2841 (2004).
Takahashi et al., "Development of chemically stable solid phases for the target isolation with reduced nonspecific binding proteins," *Bioorganic & Medicinal Chemistry Letters*, vol. 16: 447-450 (2006).
Harding et al., "A receptor for the immunosuppressant FK506 is a *cis-trans* peptidyl-prolyl isomerase," *Nature*, 341: 758-760 (1989).
Shimizu et al., "High-performance affinity beads for identifying drug receptors," *Nature Biotechnology*, 18: 877-881 (2000).
Taunton et al., "A Mammalian Histone Deacetylase Related to the Yeast Transcriptional Regulator Rpd3p," *Science*, 272: 408-411 (1996).

* cited by examiner

*Primary Examiner* — Shafiqul Haq
(74) *Attorney, Agent, or Firm* — Barnes & Thornburg LLP; Brian R. Dorn

(57) ABSTRACT

A resin which is prepared by polymerizing a monomer component incorporating a hydrophilic spacer, and a ligand-immobilized solid phase carrier obtained by immobilizing a ligand to the resin, are capable of reducing the non-specific adsorption of substances, other than the target molecule for the ligand, which mingle in the sample, to the resin and/or the ligand. Therefore, target molecule search, identification and the like with less noise are enabled.

3 Claims, 1 Drawing Sheet

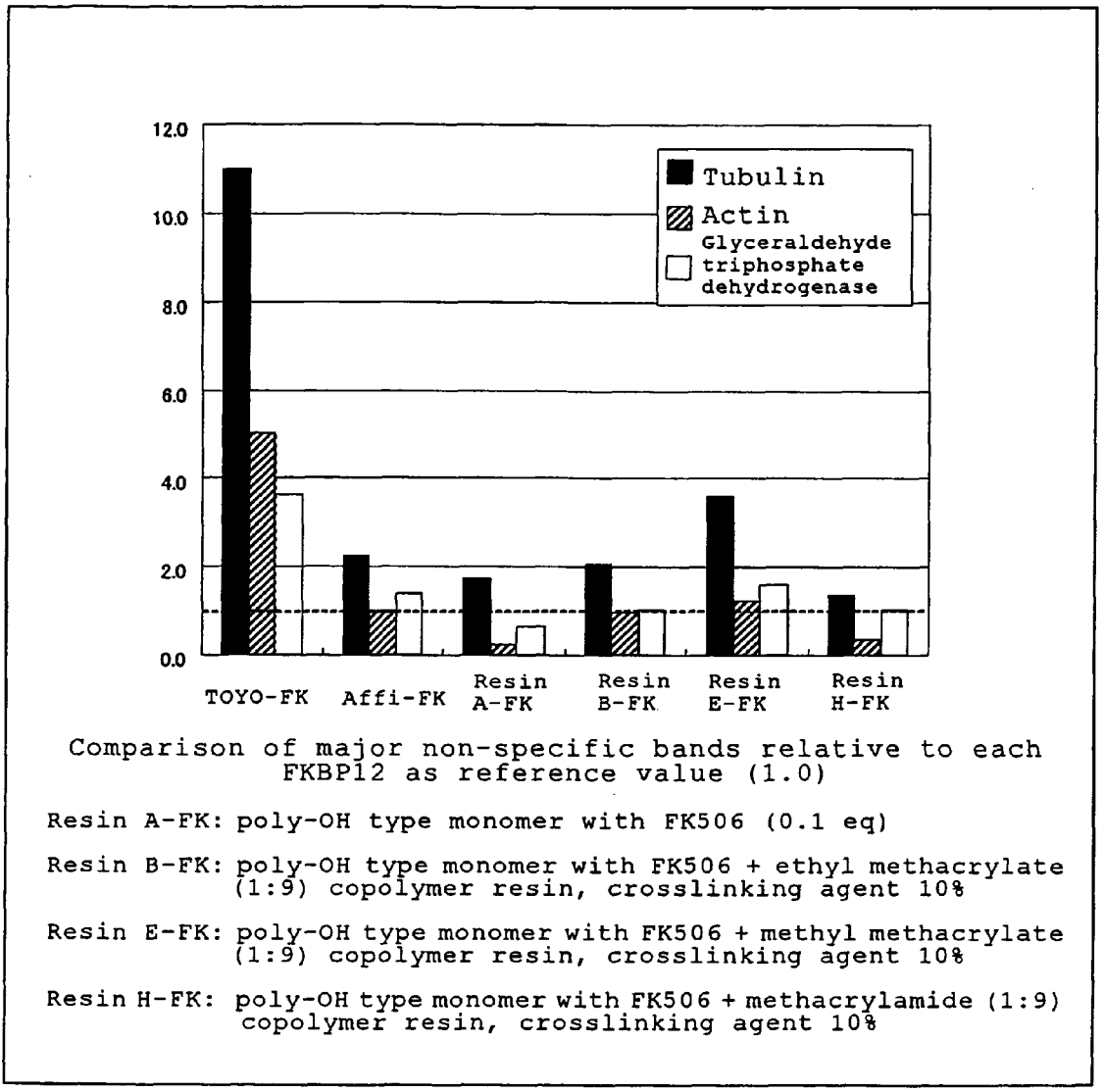

AFFINITY RESIN

CROSS-REFERENCE TO RELATED APPLICATIONS

This application is a national phase of international patent application no. PCT/JP2004/015659, filed Oct. 15, 2004, which claims the benefit of patent application nos. JP 2003-357144, filed Oct. 17, 2003, and JP 2004-178808, filed Jun. 16, 2004, all of which are herein incorporated by reference in their entirety.

TECHNICAL FIELD

The present invention relates to a resin useful as a solid phase carrier for affinity chromatography (hereinafter sometimes simply referred to as a resin for affinity) and a monomer suitable for preparing the resin. More specifically, the present invention relates to a resin for affinity that exhibits little adsorption of non-specific proteins and is highly stable.

BACKGROUND OF THE INVENTION

In recent years, there have been aggressive attempts to search a molecule that exhibits a specific interaction with a particular molecule have been actively conducted using a technique based on specific intermolecular interactions. Against this background, a method of immobilizing a low-molecular compound like a pharmaceutical exhibiting noteworthy physiological activity onto an appropriate solid phase carrier, and searching a target, is drawing attention. Since target search research using this technique called affinity resin enables efficient identification of a target for a low-molecular compound exhibiting a physiological activity of interest, many investigations have been conducted and some specific achievements have been reported. As examples of these investigations, 1) the discovery of FKBP proteins, which bind to the immunosuppressant FK506 (FK506 binding proteins), by Professor Schreiber in 1989 (discovery of FKBP12 as a protein that binds to FK506 in cells; see "Nature, UK, Oct. 26, 1989, Vol. 341, pp. 758-760"), 2) the discovery of HDAC as a target protein for the anticancer agent Trapoxin (see "Science, USA, Apr. 19, 1996, Vol. 272, pp. 408-411"), and 3) the discovery of Ref-1 as a target protein for E3330 by Handa et al. (see "Nature Biotechnology, UK, August 2000, Vol. 18, No. 8, pp. 877-881") are known well. In the area of diagnostic reagents, therapeutic efficacy increases if the presence of a lesion is non-invasively detectable as early after onset of disease as possible; therefore, for example, there are brisk research activities to identify a substance called a marker, such as a trace protein, which is specifically expressed in a particular cancer, in a collected patient blood and the like.

To date, however, in the above-described technique, the presence of non-specific proteins other than the protein involved in a specific intermolecular interaction with an immobilized ligand molecule has been problematic. The present inventors have already found that by allowing a hydrophilic spacer to interlie between a ligand and an affinity resin during the binding thereof, non-specific interactions between the immobilized ligand molecule and/or the affinity resin itself and molecules that are not specific for the ligand are reduced (Japanese Patent Application No. 2002-222226 (WO2004/025297)). However, focusing on the reduction of non-specific interactions, affinity resins having a highly hydrophilic solid phase carrier, like agarose-series affinity resins (for example, AffiGel), serve excellently as affinity resins. However, agarose-series resins are faulty in that they are not always suitable for research into a broad range of ligands because they cause irreversible denaturation due to the chemical characteristics of the constituents thereof in many systems in common use for synthesis. From the viewpoint of stability, methacrylate-series resins (for example, TOYOPEARL) are chemically stable and exhibit sufficient resistance to reactions in many organic solvents.

There has been a demand for the development of a resin having intermolecular non-specific interactions reduced to an extent comparable to that of agarose-series affinity resins, and possessing a stability comparable to that of methacrylate-series resins.

It is an object of the present invention to provide a resin capable of reducing intermolecular non-specific interactions, and possessing excellent stability, particularly an affinity resin.

BRIEF SUMMARY OF THE INVENTION

With the aim of solving the above-described problems, the present inventors conducted diligent investigations, attempted to synthesize a resin for affinity that is a methacrylate-series resin but possesses a hydrophilic characteristic comparable to that of agarose-series resins, by subjecting a methacrylate monomer incorporating an already developed hydrophilic spacer (Japanese Patent Application No. 2002-222226 (WO2004/025297)), as the resin starting material, to a polymerization reaction, succeeded in the synthesis, and developed the present invention.

Accordingly, the present invention relates to the following:
[1] A resin obtained by polymerizing a starting material monomer, wherein the monomer incorporates a hydrophilic spacer.
[2] The resin described in [1] above, wherein the monomer is a (meth)acrylic monomer.
[3] The resin described in [1] or [2] above, wherein the hydrophilic spacer has at least one partial structure represented by any one formula selected from the group consisting of the following formulas (Ia) to (Ie).

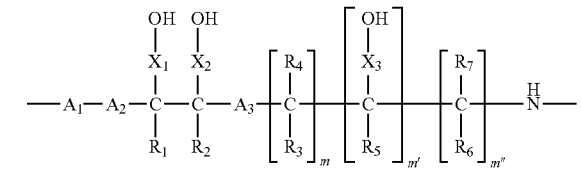

(Ia)

wherein (Ia),
$A_1$ is —O— or —NH—, $A_2$ is a single bond or a lower alkylene group, $A_3$ is an appropriate joining group,
each of $X_1$ to $X_3$, whether identical or not, is a single bond or a methylene group optionally substituted by a linear or branched alkyl group having 1 to 3 carbon atoms,
each of $R_1$ to $R_7$, whether identical or not, is a hydrogen atom, a linear or branched alkyl group having 1 to 3 carbon atoms, —CH$_2$OH or a hydroxyl group,
m is an integer of 0 to 2, m' is an integer of 0 to 10, m" is an integer of 0 to 2,
when a plurality of $R_3$ to $R_7$ units exist, they may be identical or not, and when a plurality of $X_3$ units exist, they may be identical or not;

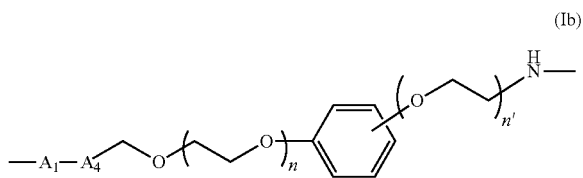
(Ib)

wherein (Ib),
$A_1$ is —O— or —NH—, $A_4$ is a lower alkylene group,
each of n and n', whether identical or not, is an integer of 1 to 10;

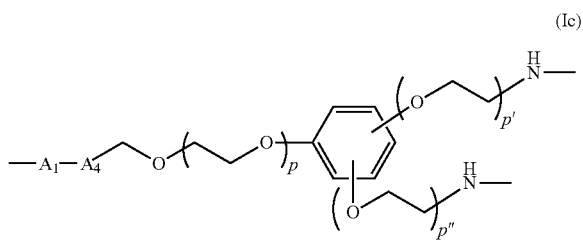
(Ic)

wherein (Ic),
$A_1$ is —O— or —NH—, $A_4$ is a lower alkylene group,
each of p, p' and p", whether identical or not, is an integer of 1 to 10;

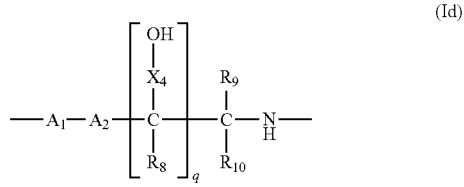
(Id)

wherein (Id),
$A_1$ is —O— or —NH—, $A_2$ is a single bond or a lower alkylene group,
$X_4$ is a single bond or a methylene group optionally substituted by a linear or branched alkyl group having 1 to 3 carbon atoms, each of $R_8$ to $R_{10}$, whether identical or not, is a hydrogen atom, a linear or branched alkyl group having 1 to 3 carbon atoms, —CH$_2$OH or a hydroxyl group,
q is an integer of 1 to 7,
when a plurality of $R_8$ units exist, they may be identical or not, and when a plurality of $X_4$ units exist, they may be identical or not;

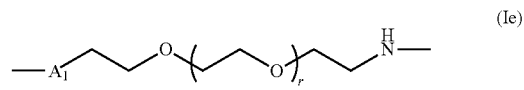
(Ie)

wherein (Ie),
$A_1$ is —O— or —NH—,
r is an integer of 1 to 10.
[4] The resin described in [3] above, wherein the hydrophilic spacer has at least one partial structure represented by the following formula (Id).

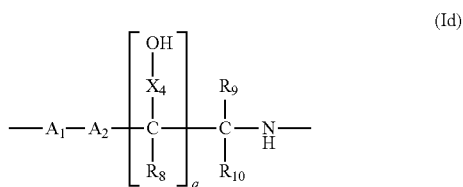
(Id)

wherein (Id),
$A_1$ is —O— or —NH—, $A_2$ is a single bond or a lower alkylene group,
$X_4$ is a single bond or a methylene group optionally substituted by a linear or branched alkyl group having 1 to 3 carbon atoms, each of $R_8$ to $R_{10}$, whether identical or not, is a hydrogen atom, a linear or branched alkyl group having 1 to 3 carbon atoms, —CH$_2$OH or a hydroxyl group,
q is an integer of 1 to 7,
when a plurality of $R_8$ units exist, they may be identical or not, and when a plurality of $X_4$ units exist, they may be identical or not.
[5] The resin described in [4] above, wherein in the formula (Id), $A_1$ is —O—, $A_2$ is a methylene group, $X_4$ is a single bond, q is 4, the plurality of $R_8$ units are identically hydrogen atoms, and $R_9$ and $R_{10}$ are hydrogen atoms.
[6] The resin described in [1] above, wherein the hydrophilic spacer is a compound represented by the formula shown below.

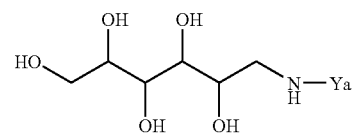

wherein Ya is a hydrogen atom or an amino-group-protecting group.
[7] The resin described in [5] above, which comprises a copolymer of a compound represented by the formula shown below.

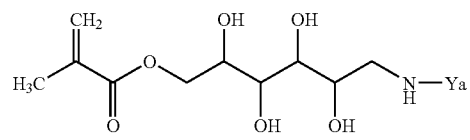

wherein Ya is a hydrogen atom or an amino-group-protecting group.
[8] A compound represented by the formula shown below.

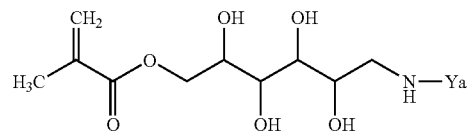

wherein Ya is a hydrogen atom or an amino-group-protecting group.
[9] The resin described in [3] above, wherein the hydrophilic spacer has at least one partial structure represented by the following formula (Ie).

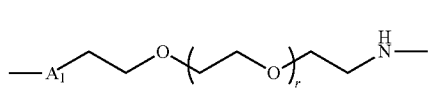

(Ie)

wherein (Ie),
$A_1$ is —O— or —NH—,
r is an integer of 1 to 10.
[10] The resin described in [9] above, wherein in the formula (Ie), $A_1$ is —O—.
[11] The resin described in [1] above, wherein the hydrophilic spacer is a compound represented by the formula shown below.

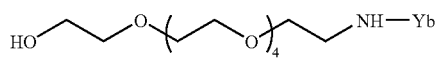

wherein Yb is a hydrogen atom or an amino-group-protecting group.
[12] The resin described in [10] above, which comprises a copolymer of a compound represented by the formula shown below.

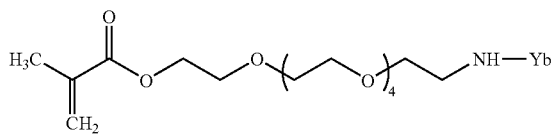

wherein Yb is a hydrogen atom or an amino-group-protecting group.
[13] A compound represented by the formula shown below.

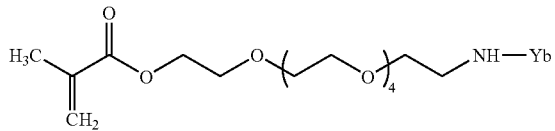

wherein Yb is a hydrogen atom or an amino-group-protecting group.
[14] The resin described in [9] above, wherein in the formula (Ie), $A_1$ is —NH—.
[15] The resin described in [1] above, wherein the hydrophilic spacer is a compound represented by the formula shown below.

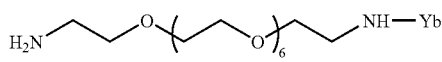

wherein Yb is a hydrogen atom or an amino-group-protecting group.
[16] The resin described in [14] above, which comprises a copolymer of a compound represented by the formula shown below.

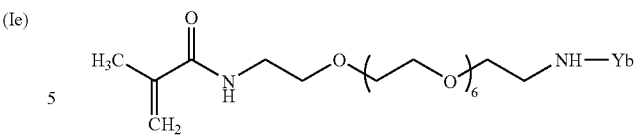

wherein Yb is a hydrogen atom or an amino-group-protecting group.
[17] A compound represented by the formula shown below.

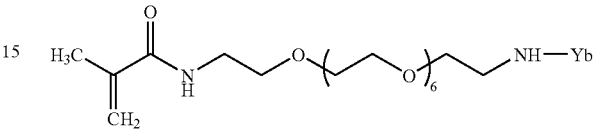

wherein Yb is a hydrogen atom or an amino-group-protecting group.
[18] A solid phase carrier for affinity chromatography comprising a ligand immobilized on the resin described in any one of [1] to [7], [9] to [12] and [14] to [16] above.
[19] The solid phase carrier described in [18] above, which is for searching a target molecule for the ligand.
[20] A screening method for a target molecule that exhibits a specific interaction with a ligand, which comprises at least the following steps:
(i) a step for immobilizing a ligand to the resin described in any one of [1] to [7], [9] to [12] and [14] to [16] above,
(ii) a step for bringing a sample comprising or not comprising a target molecule into contact with the ligand-immobilized resin obtained in (i) above,
(iii) a step for identifying and analyzing a molecule that has exhibited or has not exhibited a specific interaction with the ligand, and
(iv) a step for judging a molecule that exhibits a specific interaction with the ligand to be a target molecule on the basis of the analytical results obtained in (iii) above.
[21] A method of measuring a target molecule that exhibits a specific interaction with a ligand in a sample, which comprises at least the following steps:
(i) a step for immobilizing a ligand to the resin described in any one of [1] to [7], [9] to [12] and [14] to [16] above,
(ii) a step for bringing a sample into contact with the ligand-immobilized resin obtained in (i) above,
(iii) a step for measuring and analyzing a molecule that has exhibited or has not exhibited a specific interaction with the ligand, and
(iv) a step for measuring a target molecule that exhibits a specific interaction with the ligand on the basis of the analytical results obtained in (iii) above.

BRIEF DESCRIPTION OF THE DRAWINGS

FIG. 1 is a drawing showing the degree of the non-specific adsorption of proteins onto an FK506-immobilized solid phase carrier obtained by immobilizing a ligand (FK506) to a resin prepared by polymerizing a monomer component incorporating a hydrophilic spacer. Assuming the value for FKBP12, which is a target molecule for FK506, to be 1, the degree of the adsorption of each non-specific protein is shown relatively.

DETAILED DESCRIPTION OF THE INVENTION

The monomer used in synthesizing the resin of the present invention is not subject to limitation as to base structure, as long as it incorporates a hydrophilic spacer and is capable of forming a chemically and physically stable polymer, and it is preferably an ester or amide of (meth)acrylic acid. For convenience, a monomer incorporating a hydrophilic spacer is referred to as a hydrophilic monomer.

In the present invention, "a resin" comprises the above described polymer of a monomer, and is not subject to limitation, as long as it possesses a shape and physicochemical properties that make it normally usable in the art. For example, those possessing a shape and physicochemical properties that make them packable in a column and the like, or a shape and physical properties that make them separable from solutions by centrifugal operation, in affinity chromatography operation, are preferably used.

In the present invention, "a hydrophilic spacer" refers to a substance that becomes a group that interlies between a resin and a ligand molecule immobilized to the resin, and is hydrophilic. Degrees of hydrophilicity are described below. As used herein, "interlies" means that the hydrophilic spacer is present between a functional group in the resin constituent monomer and a functional group in the ligand. The hydrophilic spacer binds to the functional group in the monomer at one end and binds to the functional group in the ligand at the other end. Also, the hydrophilic spacer may be one obtained by sequentially binding and polymerizing two or more compounds, as long as it is eventually capable of functioning as a group that interlies between the resin and the ligand immobilized thereto. For example, when a (meth)acrylic monomer incorporating a hydrophilic spacer is prepared as a hydrophilic monomer, incorporation of the hydrophilic spacer in the monomer is based on a covalent bond or non-covalent bond of an amide, ester or the like synthesized by a reaction of an acrylic or methacrylic acid halide and the corresponding hydrophilic spacer, or an ordinary amide binding or ester formation reaction with acrylic acid or methacrylic acid, all of which bonds are formed using materials and reactions known in the art.

The hydrophilic spacer used in the present invention is not subject to limitation, as long as it alters the hydrophobic property of the surface of the obtainable resin to eliminate or suppress non-specific intermolecular interactions, and it is preferably one having a hydrogen bond acceptor (HBA) number of 2 or more and a hydrogen bond donor (HBD) number of 1 or more, while in a state bound to a resin (more specifically a resin-constituting monomer) and a ligand (a hydrophilic spacer in this state is hereinafter referred to as "a hydrophilic spacer portion" for convenience); normally, the HBA number is about 2 to 12, and the HBD number is about 1 to 12. More preferably, the hydrophilic spacer is a compound having an HBA number of 6 or more and an HBD number of 5 or more, or a sum of the HBA number and HBD number per molecule of the spacer of 9 or more, while in a state bound to the resin and the ligand. Also, the hydrophilic spacer may be a compound that meets two or all of these conditions.

Here, hydrogen bond acceptor number (HBA number) is the total number of nitrogen atoms (N) and oxygen atoms (O) contained, and hydrogen bond donor number (HBD number) is the total number of NH and OH contained (C. A. Lipinski et al., Advanced Drug Delivery Reviews, 23(1997), 3-25). In the present invention, even if it interlies between a resin and a ligand, the N and O or NH or OH derived from a starting material compound for monomer synthesis, such as methacrylic chloride, are not included in the HBA number or HBD number, respectively. Furthermore, even if it is derived from a hydrophilic spacer, the N and O or NH and OH derived from the amino group or hydroxyl group utilized directly in the binding to methacrylic chloride and the like are also not included in the HBA number or HBD number, respectively. To make the binding of the ligand and the hydrophilic spacer more easier, an optionally chosen group, between the ligand and the hydrophilic spacer, can be bound or introduced to the ligand in advance before it is immobilized (the group is also referred to as a linker); however, because these are chosen as appropriate depending on the ligand, and are considered to make only a little contribution to the modification of the hydrophobic property of the solid phase carrier, the N and O or NH and OH contained in the group are also not included in the HBD number or HBA number in the present invention. Note that introduction of the linker utilizes various covalent bonds or non-covalent bonds such as amide bonds, condensation, Schiff bases, C—C bonds, ester bonds, hydrogen bonds, and hydrophobic interactions, all of which are achieved using materials and reactions known in the art.

Under the circumstances of the invention of this application, the HBA number of the hydrophilic spacer is 2 or more (normally 2 to 12), and the HBD number is 1 or more (normally 1 to 12). To suppress non-specific interactions sufficiently, at least one, preferably 2 or more, of the conditions of (i) an HBA number of 6 or more, (ii) an HBD number of 5 or more, and (iii) a sum of the HBA number and the HBD number of 9 or more, are met. In the present invention, the upper limit of the HBD number or HBA number of the hydrophilic spacer is not subject to limitation, as long as it is eventually possible to polymerize a monomer incorporating the hydrophilic spacer to synthesize a resin, and each number is normally about 12, as described above.

Furthermore, the hydrophilic spacer used in the present invention is preferably one that does not exhibit a non-specific interaction (for example, protein adsorption to the spacer and the like) per se. Specifically, it is preferable that the spacer does not have a functional group that becomes positively or negatively charged in an aqueous solution; as the functional group, an amino group (but excluding cases wherein a functional group that attenuates the basicity of the amino group (for example, a carbonyl group, a sulfonyl group) is bound to the amino group), a carboxyl group, a sulfuric acid group, a nitric acid group, a hydroxamic acid group and the like can be mentioned. Here, "in an aqueous solution" specifically refers to an environment wherein a process to analyze the interaction between the ligand and the target molecule on the solid phase, a process to select the target molecule, or a binding reaction (a reaction based on a specific interaction) of the ligand and the target molecule performed to screen for the target molecule is conducted, and whereunder the hydrophilic spacer ionizes when having a functional group that becomes positively or negatively charged. Such conditions are, for example, "in an aqueous solution, pH 1 to 11, temperature 0° C. to 100° C.", preferably "nearly neutral (pH 6 to 8) pH, about 4° C. to about 40° C.".

For example, the hydrophilic spacer of the present invention is a compound having at least one of the partial structures represented by any one formula selected from the group consisting of the following formulas (Ia) to (Ie).

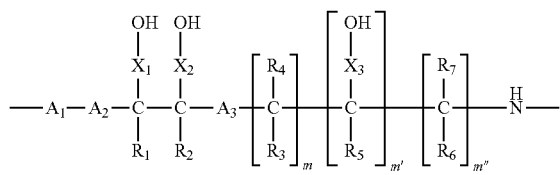

(Ia)

wherein (Ia),
$A_1$ is —O— or —NH—, $A_2$ is a single bond or a lower alkylene group, $A_3$ is an appropriate joining group,
each of $X_1$ to $X_3$, whether identical or not, is a single bond or a methylene group optionally substituted by a linear or branched alkyl group having 1 to 3 carbon atoms,
each of $R_1$ to $R_7$, whether identical or not, is a hydrogen atom, a linear or branched alkyl group having 1 to 3 carbon atoms, —CH$_2$OH or a hydroxyl group,
m is an integer of 0 to 2, m' is an integer of 0 to 10, m" is an integer of 0 to 2,
when a plurality of $R_3$ to $R_7$ units exist, they may be identical or not, and when a plurality of $X_3$ units exist, they may be identical or not;

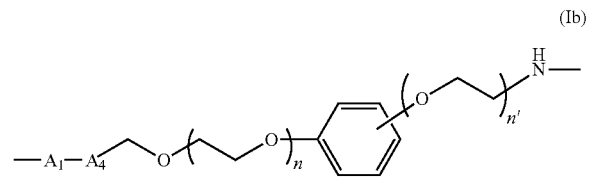

(Ib)

wherein (Ib),
$A_1$ is —O— or —NH—, $A_4$ is a lower alkylene group,
each of n and n', whether identical or not, is an integer of 1 to 10;

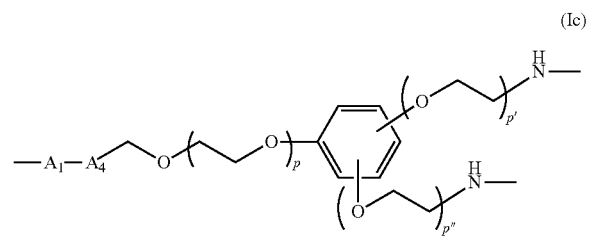

(Ic)

wherein (Ic),
$A_1$ is —O— or —NH—, $A_4$ is a lower alkylene group,
each of p, p' and p", whether identical or not, is an integer of 1 to 10;

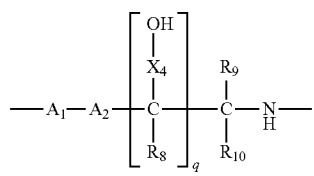

(Id)

wherein (Id),
$A_1$ is —O— or —NH—, $A_2$ is a single bond or a lower alkylene group,
$X_4$ is a single bond or a methylene group optionally substituted by a linear or branched alkyl group having 1 to 3 carbon atoms,
each of $R_8$ to $R_{10}$, whether identical or not, is a hydrogen atom, a linear or branched alkyl group having 1 to 3 carbon atoms, —CH$_2$OH or a hydroxyl group,
q is an integer of 1 to 7,
when a plurality of $R_8$ units exist, they may be identical or not, and when a plurality of $X_4$ units exist, they may be identical or not;

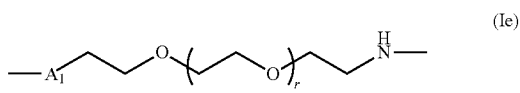

(Ie)

wherein (Ie),
$A_1$ is —O— or —NH—,
r is an integer of 1 to 10.

In the definition of each group in this description, "a lower alkylene group" means a linear or branched alkylene group having 1 to 6 carbon atoms; specifically, methylene group, ethylene group, propylene group, isopropylene group, butylene group, isobutylene group, sec-butylene group, tert-butylene group, pentylene group, isopentylene group, neopentylene group, tert-pentylene group, hexylene group, isohexylene group and the like can be mentioned.

As examples of "a linear or branched alkyl group having 1 to 3 carbon atoms", methyl group, ethyl group, propyl group, isopropyl group and the like can be mentioned.

In this description, "a methylene group optionally substituted by a linear or branched alkyl group having 1 to 3 carbon atoms" means a non-substituted methylene group and a methylene group mono- or di-substituted by the above-described linear or branched alkyl groups having 1 to 3 carbon atoms.

"An appropriate joining group" is not subject to limitation, as long as it is capable of joining mutually adjoining sites; specifically, the following groups are used.

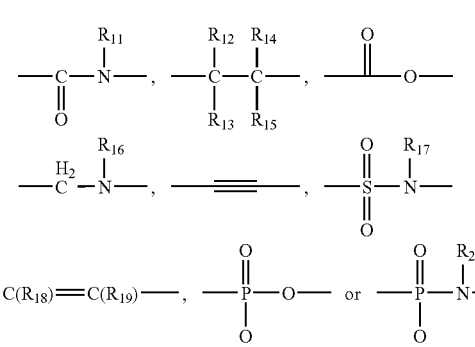

(In the formulas, $R_{11}$ is a hydrogen atom or a linear or branched alkyl group having 1 to 3 carbon atoms, each of $R_{12}$ to $R_{15}$, whether identical or not, is a hydrogen atom, a linear or branched alkyl group having 1 to 3 carbon atoms, —CH$_2$OH or a hydroxyl group, each of $R_{16}$ to $R_{20}$, whether identical or not, is a hydrogen atom, a linear or branched alkyl group having 1 to 3 carbon atoms (the alkyl group is optionally substituted by a hydrophilic substituent such as a hydroxyl group, a carboxylic acid group, or an amino group)).

A general method of producing a hydrophilic spacer that can be incorporated in the monomer in the present invention is described below, but it is obvious to those skilled in the art that the same can also be produced by other methods commonly performed in the art or combinations thereof.

Note that the abbreviations used in this description are as follows.

| Abbreviation | Formal designation |
| --- | --- |
| Ac | Acetyl group |
| AET | Aminoethyltartaric diamide |
| AIBN | Azobisisobutyronitrile |
| AMT | Aminomethyltartaric diamide |
| Boc | tert-Butoxycarbonyl |
| Boc$_2$O | Di-tert-butyl dicarbonate |
| Bn | Benzyl group |
| Bu$_3$P | Tributylphosphine |
| CDI | 1,1'-Carbonyldiimidazole |
| DABT | Dihydroxyaminobutyltartaric acid |
| DBU | 1,8-Diazabicyclo[5.4.0]undeca-7-ene |
| DMAP | Dimethylaminopyridine |
| DME | 1,2-Dimethoxyethane |
| DMF | Dimethylformamide |
| EDC | 1-[3-(Dimethylamino)propyl]-3-ethylcarbodiimide |
| Et | Ethyl group |
| Fmoc | 9-Fluorenylmethyloxycarbonyl group |
| Fmoc-OSu | 9-Fluorenylmethylsuccinimidylcarbonate |
| HOBt | 1-Hydroxybenzotriazole |
| HyT | Hydrazinotartaric amide |
| Me | Methyl group |
| NMP | N-methyl-2-pyrrolidone |
| PEG | Polyethylene glycol |
| Ph$_3$P | Triphenylphosphine |
| PyBOP | Benzotriazol-1-yl-oxy-tris-pyrrolidino-phosphonium hexafluorophosphate |
| TBAF | Tetrabutylammonium fluoride |
| TBDMS | tert-Butyldimethylsilyl group |
| TBDMSOTf | Trifluoromethanesulfonic acid tert-butyldimethylsilyl group |
| TBDPS | tert-Butyldiphenylsilyl group |
| TBS | tert-Butyldimethylsilyl group |
| tBu | tert-Butyl group |
| TFA | Trifluoroacetic acid |
| THF | Tetrahydrofuran |
| TMAD | N,N,N',N'-tetramethylazodicarboxamide |
| TOYO-Pearl resin | TOYO-Pearl resin |
| Tr | Trityl group |
| Ts | Tosyl group (toluenesulfonyl group) |
| WSC | Water-soluble carbodiimide (N-ethyl-N'-(3'-dimethylaminopropyl)carbodiimide) |

Process 1: Production Method (1) for a Hydrophilic Spacer Having a Partial Structure Represented by the General Formula (Ia) (m=1, m'=2, m"=1)

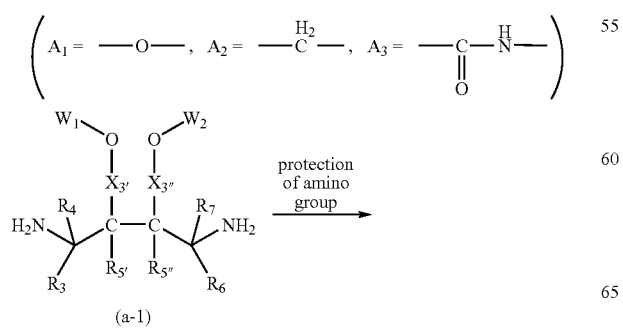

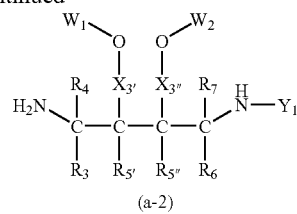
(a-2)

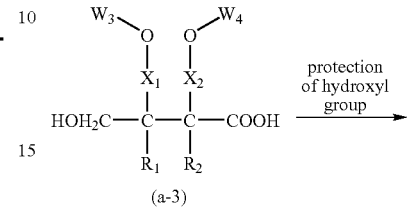
(a-3)

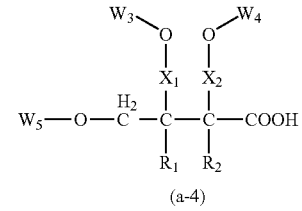
(a-4)

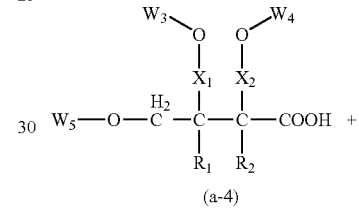
(a-4)

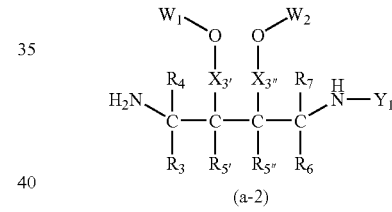
(a-2)

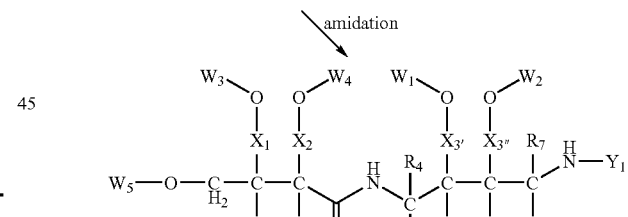
(a-5)

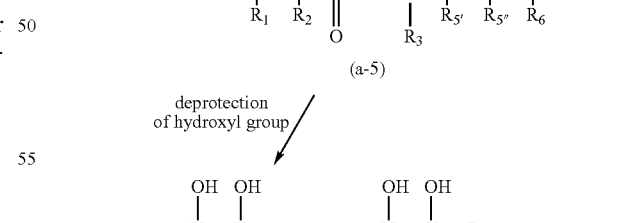
(a-6)

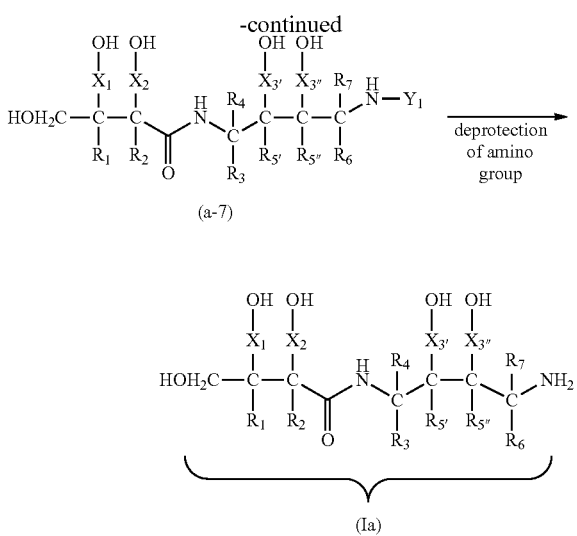

(a-7)

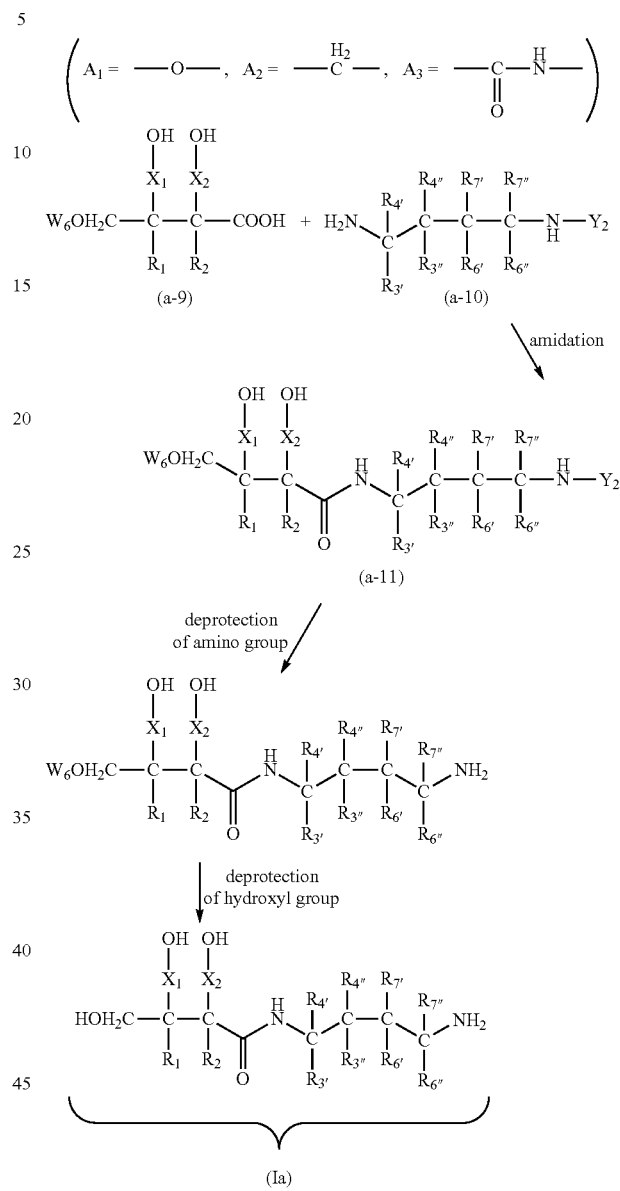

In the formulas, $W_1$ to $W_5$ are hydroxyl-group-protecting groups, and $Y_1$ is an amino-group-protecting group. $X_{3'}$ has the same definition as $X_3$, and $X_{3''}$ has the same definition as $X_3$. $R_{5'}$ has the same definition as $R_5$, and $R_{5''}$ has the same definition as $R_5$. The definitions for the other individual symbols are as described above.

As the hydroxyl-group-protecting group, an optionally chosen group in common use in the art is used; specifically, alkyl groups such as tert-butyl group; acyl groups such as acetyl group, propionyl group, pivaloyl group and benzoyl group; alkoxycarbonyl groups such as methoxycarbonyl group and tert-butoxycarbonyl group; aralkyloxycarbonyl groups such as benzyloxycarbonyl group; arylmethyl groups such as benzyl group and naphthylmethyl group; silyl groups such as trimethylsilyl group, triethylsilyl group, tert-butyldimethylsilyl group and tert-butyldiphenylsilyl group; lower alkoxymethyl groups such as ethoxymethyl group and methoxymethyl group, and the like can be mentioned as examples, with preference given to tert-butyldimethylsilyl group, tert-butyldiphenylsilyl group, methoxymethyl group, and tert-butyl group. As the amino-group-protecting group, an optionally chosen group in common use in the art is used; specifically, lower alkoxycarbonyl groups such as tert-butoxycarbonyl group and methoxycarbonyl group; aralkyloxycarbonyl groups such as benzyloxycarbonyl group; aralkyl groups such as benzyl group; substituted sulfonyl groups such as benzenesulfonyl group, p-toluenesulfonyl group and methanesulfonyl group, and the like can be mentioned as examples, with preference given to tert-butoxycarbonyl group and benzyloxycarbonyl group.

Amino group protection and deprotection and hydroxyl group protection and deprotection can be performed as appropriate using known methods and reagents according to the protective group used.

A reaction to dehydrate-condense compound (a-4) (carboxylic acid) and compound (a-2) (amino body) by amidation is normally carried out in the presence of an equivalent of the amino body and carboxylic acid, using about 1.1 equivalents of a condensing agent such as N-ethyl-N'-dimethylaminocarbodiimide or N-hydroxy-benzotriazole in a solvent such as DMF or methylene chloride at room temperature for about 1 hour to 10 hours.

Process 2: Production Method (2) for a Hydrophilic Spacer Having a Partial Structure Represented by the General Formula (Ia) (m=2, m'=0, m''=2)

In the formulas, $Y_2$ is an amino-group-protecting group. $W_6$ is a hydroxyl-group-protecting group. $R_{3'}$ has the same definition as $R_3$, and $R_{3''}$ has the same definition as $R_3$. $R_{4'}$ has the same definition as $R_4$, and $R_{4''}$ has the same definition as $R_4$. $R_{6'}$ has the same definition as $R_6$, and $R_{6''}$ has the same definition as $R_6$. $R_{7'}$ has the same definition as $R_7$, and $R_{7''}$ has the same definition as $R_7$. The definitions for the other individual symbols are as described above. As the amino-group-protecting group, the same examples as those described above can be mentioned. Amino group deprotection can be performed as appropriate using known methods and reagents according to the protective group used.

A reaction to dehydrate-condense compound (a-9) (carboxylic acid) and compound (a-10) (amino body) by amidation is normally carried out in the presence of an equivalent of the amino body and carboxylic acid, using about 1.1 equivalents of a condensing agent such as N-ethyl-N'-dimethylaminocarbodiimide or N-hydroxy-benzotriazole in a solvent such as DMF or methylene chloride at room temperature for about 1 hour to 10 hours.

Process 3: Production Method (3) for a Hydrophilic Spacer Having a Partial Structure Represented by the General Formula (Ia) (m=1, m'=0, m"=0)

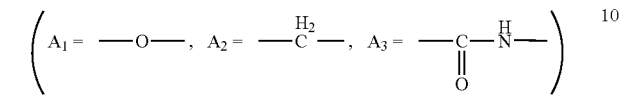

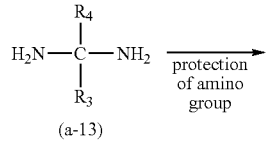

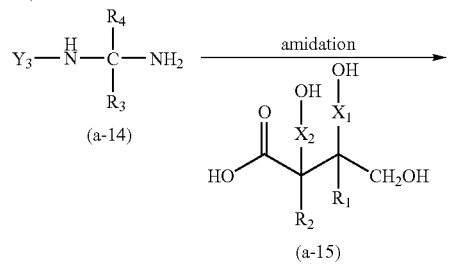

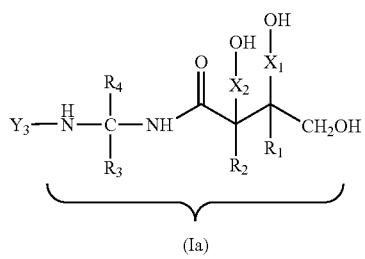

In the formulas, $Y_3$ is an amino-group-protecting group, and the definitions for the other individual symbols are as described above. As the amino-group-protecting group, the same examples as those described above can be mentioned.

A reaction to dehydrate-condense compound (a-14) (amino body) and compound (a-15) (carboxylic acid) by amidation is normally carried out in the presence of an equivalent of the amino body and carboxylic acid, using about 1.1 equivalents of a condensing agent such as N-ethyl-N'-dimethylaminocarbodiimide or N-hydroxy-benzotriazole in a solvent such as DMF or methylene chloride at room temperature for about 1 hour to 10 hours.

Process 4: Production Method for a Hydrophilic Spacer Having a Partial Structure Represented by the General Formula (Ib) (n–1=n'–1=$n_2$)

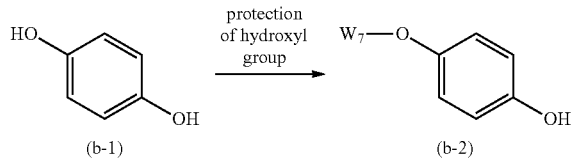

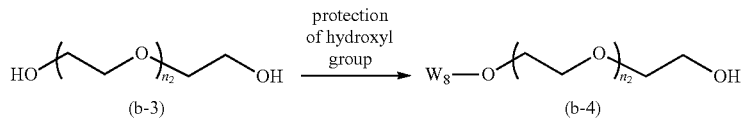

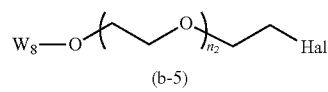

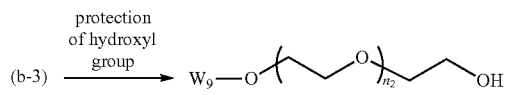

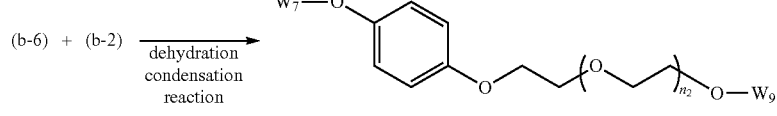

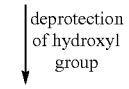

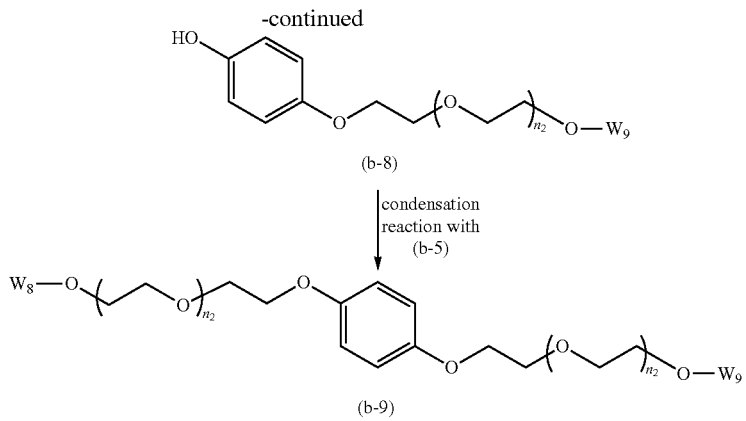

(b-8)

↓ condensation reaction with (b-5)

(b-9)

In the formulas, $W_7$ to $W_9$ are hydroxyl-group-protecting groups, Hal represents a halogen atom (chlorine atom, bromine atom, iodine atom, fluorine atom), and the definitions for the other individual symbols are as described above. As the hydroxyl-group-protecting group, the same examples as those described above can be mentioned. Note that $n_2$ is n−1 or n'−1 (n and n' are as described above).

Hydroxyl group protection and deprotection are performed as appropriate using known methods and reagents according to the protective group used.

A halogen substitution reaction of compound (b-4) (alcohol body) to compound (b-5) is normally performed by reacting 1 equivalent of the alcohol body with 2 to 3 equivalents of carbon tetrabromide and 1 to 2 equivalents of triphenylphosphine in a solvent such as methylene chloride at 0° C. to room temperature for 1 hour to several hours.

A dehydration-condensation reaction of compound (b-6) (alcohol body) and compound (b-2) (phenol body) is normally performed by reacting 1 equivalent of the alcohol body and 1 equivalent of tributylphosphine in toluene solvent at room temperature for about 1 hour, adding thereto 1 equivalent of the phenol body and a condensing agent such as 1,1'-azobis(N,N-dimethylformamide), and carrying out the reaction at 0 to 50° C. for several hours to overnight.

A condensation reaction of compound (b-8) (phenol body) and compound (b-5) (halogen body) is normally performed by reacting 1 equivalent of the phenol body and about 10-fold equivalents of a strong base like sodium hydride in excess in a solvent such as THF at 0 to 10° C. for about 10 to 60 minutes, adding thereto about 2 equivalents of the halogen body, and carrying out the reaction at room temperature for about 1 to 10 hours.

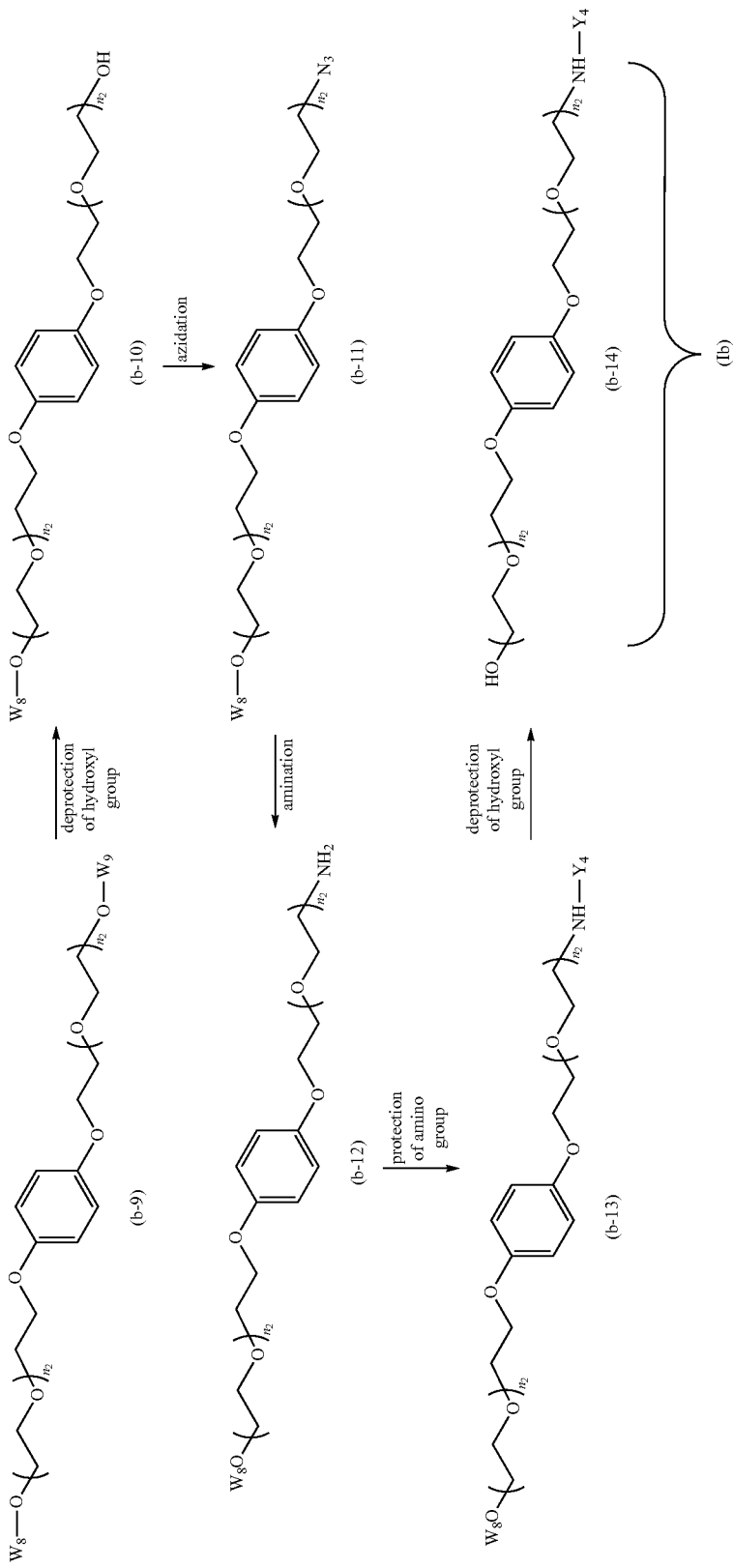

In the formulas, $Y_4$ is an amino-group-protecting group, and the definitions for the other individual symbols are as described above. As the hydroxyl-group-protecting group and the amino-group-protecting group, the same examples as those described above can be mentioned.

Hydroxyl group or amino group deprotection is performed as appropriate using known methods and reagents according to the protective group used.

Azidation of compound (b-1) (alcohol body) to compound (b-11) is normally performed by reacting 1 equivalent of the alcohol body, about 1.5 equivalents of p-toluenesulfonyl chloride and about 0.2 equivalents of a base like 4-dimethylaminopyridine in a solvent such as pyridine at 30 to 50° C. for several hours to yield an O-tosyl body, isolating the O-tosyl body, adding thereto about 10-fold equivalents of sodium azide in excess, and carrying out the reaction in a solvent such as DMF at 50 to 90° C. for several hours.

Amination of compound (b-11) (azide body) to compound (b-12) is normally achieved by reacting 1 equivalent of the azide body using about 0.1 equivalent of a catalyst like palladium hydroxide in the presence of a solvent such as methanol and in the presence of 1 to several atmospheric pressures of hydrogen at room temperature for several hours.

Process 5: Production Method for a Hydrophilic Spacer Having a Partial Structure Represented by the General Formula (Ic)

In each structural formula, particular groups and particular compounds are shown in some cases, which, however, are given for exemplification and are not to be construed as limiting. They are variable as appropriate, as long as function equivalently.

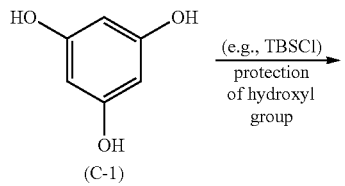

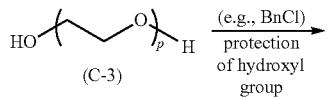

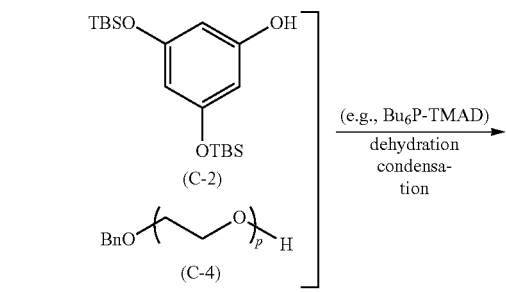

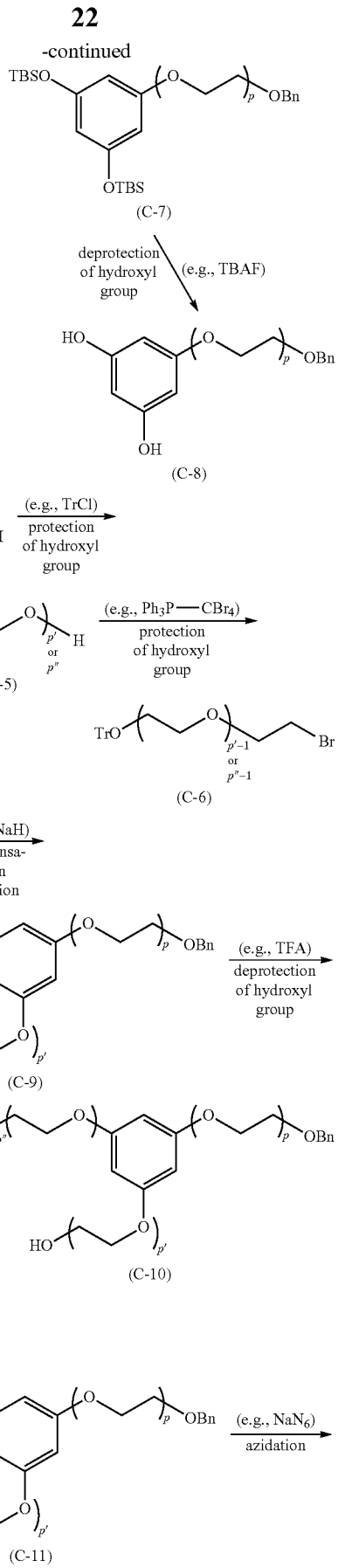

-continued

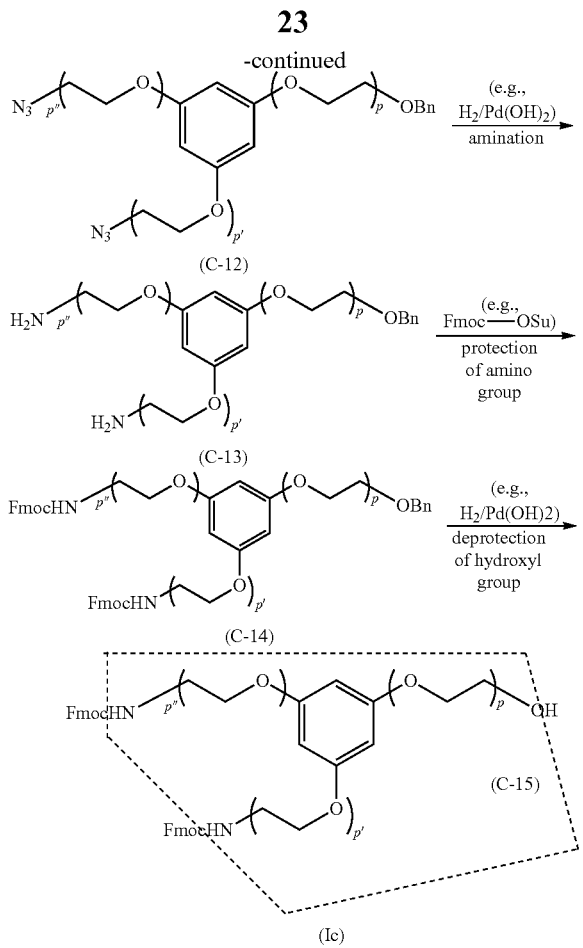

In the formulas, the definitions for the individual symbols are as described above. The hydroxyl-group-protecting groups, amino-group-protecting groups and carboxyl-group-protecting groups in the formulas are given for exemplification, in addition to which groups optionally chosen groups in common use in the art are used. Specifically, the same examples as those described above can be mentioned. It will be obvious to those skilled in the art that amino group protection, carboxyl group deprotection, and hydroxyl group protection and deprotection can be performed as appropriate using known methods and reagents according to the protective group used, in addition to those described herein.

Hydroxyl group protection of compound (c-1) (phenol body) to compound (c-2), when using TBS, for example, as the protecting group, is normally performed by reacting 1 equivalent of the phenol body, about 3 equivalents of a base (for example, imidazole) and about 2 equivalents of silyl chloride in a solvent such as DMF at room temperature for about 10 hours.

A dehydration-condensation reaction of compound (c-2) (phenol body) and compound (c-4) (alcohol body) is normally performed by reacting 1 equivalent of the alcohol body and 1 equivalent of tributylphosphine in toluene solvent at room temperature for about 1 hour, adding thereto 1.3 equivalents of the phenol body and 1.3 equivalents of a condensing agent such as 1,1'-azobis(N,N-dimethylformamide), and carrying out the reaction at room temperature for several hours to overnight.

Hydroxyl group deprotection of compound (c-7) (phenol-protected body) to compound (c-8) is normally performed by reacting 1 equivalent of the phenol-protected body (for example, silyl-protected body) and about 1.2 equivalents of tetrabutylammonium fluoride in a solvent such as THF at room temperature for about 1 hour.

A condensation reaction of compound (c-8) (phenol body) and compound (c-6) (halide) is normally performed by reacting 1 equivalent of the phenol body and about 5.2 equivalents of a strong base such as sodium hydride in excess in a solvent such as THF or DMF at room temperature for about 10 to 60 minutes, adding thereto about 4 equivalents of the halide (for example, alkyl bromide), and carrying out the reaction at room temperature for about 4 hours. By this condensation reaction, compound (c-9) is obtained.

Hydroxyl group deprotection of compound (c-9) (phenol-protected body) to compound (c-10) (alcohol body) is normally performed by reacting 1 equivalent of the phenol-protected body (for example, trityl-protected body) in a solvent such as TFA-containing methylene chloride at room temperature for about 1 hour.

A hydroxyl group tosylation reaction of compound (c-10) (alcohol body) to compound (c-11), when using Ts, for example, as the protecting group, is normally performed by reacting 1 equivalent of the alcohol body, a catalytic amount of a base such as DMAP, and about 6 equivalents of tosyl chloride in a solvent such as pyridine at room temperature to 40° C. for about 2 hours.

Azidation of compound (c-11) (tosyl body) to compound (c-12) is performed by reacting 1 equivalent of the tosyl body and about 15 equivalents of sodium azide in a solvent such as DMF at about 60° C. for about 2 hours.

Amination of compound (c-12) (phenol-protected body) to compound (c-13) and introduction of an amino-group-protecting group to compound (c-14) are normally performed by reacting 1 equivalent of the phenol-protected body (benzyl-protected body) and a catalytic amount of palladium hydroxide in a gaseous hydrogen atmosphere in a solvent such as methanol at room temperature about 1 hour to yield an amine body (c-13), adding thereto an about 0.84 equivalents of 9-fluorenylmethylsuccinimidyl carbonate and about 1.5 equivalents of a base like triethylamine, and carrying out the reaction in a solvent such as THF at room temperature for about 1 hour.

Hydroxyl group deprotection of compound (c-14) (hydroxyl-group-protected body) to compound (c-15) is normally achieved by reacting 1 equivalent of the hydroxyl-group-protected body (for example, benzyl-protected body) using about 0.1 equivalent of a catalyst like palladium hydroxide in the presence of a solvent such as methanol and in the presence of 1 to several atmospheric pressures of hydrogen at room temperature for several hours.

Process 6: Production Method for a Hydrophilic Spacer Having a Partial Structure Represented by the General Formula (Id) ($R_{10}=R_9$=Hydrogen Atom, $R_8$=Hydrogen Atom, $X_4$=Single Bond)

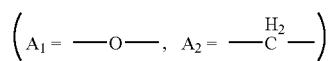

In each structural formula, particular groups and particular compounds are shown in some cases, which, however, are given for exemplification and are not to be construed as limiting. They are variable as appropriate, as long as they function equivalently. Note that a compound of the following formula (d-1) is commercially available.

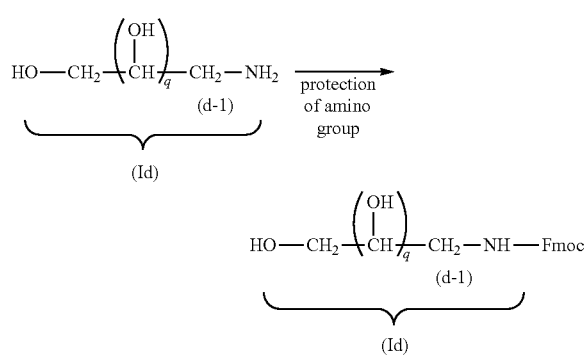

In the formulas, the definitions for the individual symbols are as described above. The amino-group-protecting group in the formulas is given for exemplification, in addition to which groups optionally chosen groups in common use in the art are used. Specifically, the same examples as those described above can be mentioned. Amino group protection can be performed as appropriate using known methods and reagents according to the protective group used.

Process 7: Production Method for a Hydrophilic Spacer Having a Partial Structure Represented by the General Formula (Ie)

In each structural formula, particular groups and particular compounds are shown in some cases, which, however, are given for exemplification and are not to be construed as limiting. They are variable as appropriate, as long as they function equivalently. Note that compounds of the following formulas (e-1) and (e-1)' are commercially available.

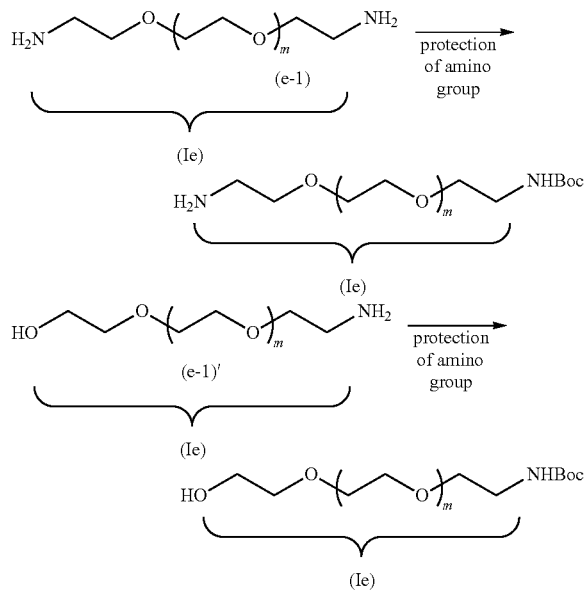

In the formulas, the definitions for the individual symbols are as described above. The amino-group-protecting groups in the formulas are given for exemplification, in addition to which groups optionally chosen groups in common use in the art are used. Specifically, the same examples as those described above can be mentioned. Amino group protection can be performed as appropriate using known methods and reagents according to the protective group used.

The hydrophilic spacer used in producing the resin of the present invention is preferably one having at least one partial structure represented by the formula (Id) or the formula (Ie), with preference given to a hydrophilic spacer wherein in the formula (Id), $A_1$ is —O—, $A_2$ is a lower alkylene group (particularly a methylene group), the plurality of $X_4$ units are identically single bonds, q is 4, the plurality of $R_8$ units are identically hydrogen atoms, and $R_9$ and $R_{10}$ are hydrogen atoms. More specifically, a resin comprising a polymer of a hydrophilic monomer prepared by incorporating a compound represented by one of the following formulas:

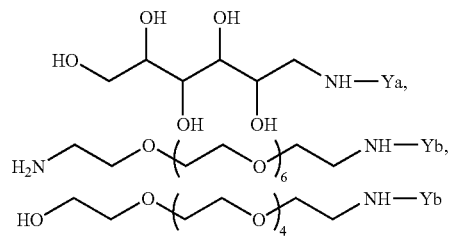

(in the formulas, Ya and Yb are hydrogen atoms or amino-group-protecting groups) into the above-described monomer (preferably a (meth)acrylic monomer), is suitably used in the present invention.

As examples of a monomer incorporating a hydrophilic spacer (that is, a hydrophilic monomer), the following compounds can be mentioned.

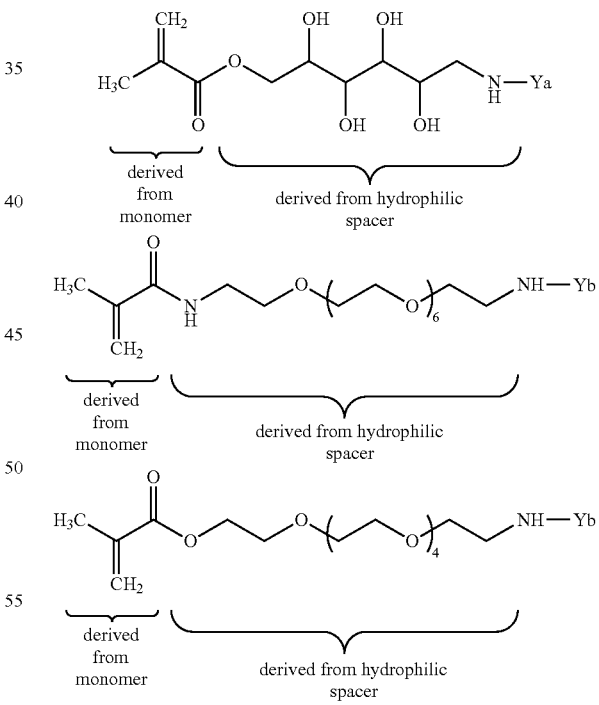

(In the formulas, Ya and Yb are hydrogen atoms or amino-group-protecting groups.)

The resin of the present invention is obtained by polymerizing the hydrophilic monomer of the present invention. As examples of the method of polymerization, solution polymerization, emulsion polymerization, dispersion polymerization, suspension polymerization, solid phase polymerization (Society of Polymer Science, Japan edt., "Kobunshi Kagaku Jikkenhou", Tokyo Kagaku Dojin, ISBN 4-8079-0180) and the like can be mentioned. In these methods of polymerization, commonly known additives may be used. For example, as polymerization initiators, organic peroxides such as benzoyl peroxide and tert-butyl hydroperoxide, azo compounds such as azobisisobutyronitrile, and the like can be mentioned. In the case of emulsion polymerization, a surfactant is additionally required; for example, nonionic surfactants (for example, polyoxyethylene alkyl ethers, polyoxyalkylene alkyl ethers, polyoxyethylene derivatives, polyoxyethylene alkylamines, polyoxyethylene fatty acid esters, glycerine fatty acid esters, sorbitan fatty acid esters and the like), anionic surfactants (for example, fatty acid salts, alkylphosphates, alkylsulfuric acid ester salts, alkylbenzenesulfonates, alkylnaphthalenesulfonates, alkyldiphenyl ether disulfonates and the like) and the like can be mentioned, and these may be used in combination. In the case of suspension polymerization, a dispersion stabilizer may be further added; as examples of the dispersion stabilizer, water-soluble high-molecular compounds like polyvinyl alcohol and polyacrylates can be mentioned. Also, as required, a crosslinking agent such as glycerol dimethacrylate (CAS=[1830-78-0]), triethylene glycol dimethacrylate (CAS=[109-17-1]) or para-divinylbenzene (CAS=[1321-74-0]) is added.

When polymerization is performed in a multi-phase state involving an organic phase, a water phase and the like, such as suspension polymerization or dispersion polymerization, an organic solvent must be assessed and chosen as appropriate according to the kind of hydrophilic monomer used, particularly the kind of previously introduced hydrophilic spacer, and it is preferable to use an organic solvent that meets the requirements shown below.

Water-insoluble.
Capable of dissolving the hydrophilic monomer.
Having a boiling point of 70° C. or higher.

When a polymerization initiator and a crosslinking agent, for example, are used as ingredients subjected to the polymerization reaction, in addition to the hydrophilic monomer; the ratio thereof is normally 0.1% to 10% by weight, preferably 1% to 3% by weight, of the polymerization initiator, and normally 1% to 20% by weight, preferably 1% to 5% by weight, of the crosslinking agent, relative to 100% by weight of the hydrophilic monomer. It is also preferable to add 20% or more of a crosslinking agent; normally, up to about 90% of a crosslinking agent can be added. Although various conditions of the polymerization reaction vary depending on the kind of polymerization reaction utilized and the like, all are known in the art; for example, after being purged with an inert gas such as gaseous nitrogen, a mixture of the above-described ingredients is heated to a temperature of 70 to 100° C., and the reaction is normally carried out for 3 to 10 hours (Society of Polymer Science, Japan, edt., "Kobunshi Kagaku Jikkenhou", Tokyo Kagaku Dojin, ISBN 4-8079-0180).

In addition to the hydrophilic monomer, polymerization initiator and crosslinking agent, additives such as colorant, ultraviolet absorbent, thermal stabilizer, polymerization inhibitor, antistatic agent, and filling agent can be added as necessary.

Also, regarding the resin obtained by polymerizing the hydrophilic monomer, if the excess ligand binding caused by the excess free amino groups on the surface thereof results in an alteration of the physical properties of the resin, a treatment such as acetyl capping may be performed on the free amino groups to reduce the bindability with the ligand.

Although the resin of the present invention may comprise a polymer of the hydrophilic monomer only, it may also be a polymer of a monomer mixture obtained by mixing a given amount of a monomer having no free amino groups to prevent excess ligand binding, as described above. As such monomers, various monomer compounds in common use in the art that serve as resin starting materials can be mentioned. Preferably, the monomer is a (meth)acrylic monomer enabling the synthesis of a resin having excellent chemical stability and physical stability. As examples of the (meth)acrylic monomer, methyl(meth)acrylate, ethyl(meth)acrylate, propyl (meth)acrylate, butyl (meth)acrylate, 2-ethylhexyl(meth) acrylate, lauryl (meth)acrylate, stearyl(meth)acrylate, cyclohexyl (meth)acrylate, 2-hydroxyethyl(meth)acrylate, 2-propyl (meth)acrylate, chloro-2-hydroxyethyl(meth)acrylate, diethylene glycol mono(meth)acrylate, methoxyethyl (meth)acrylate, glycidyl(meth)acrylate, dicyclopentanyl (meth)acrylate, dicyclopentenyl(meth)acrylate and isobornyl (meth)acrylate and the like can be mentioned.

Furthermore, the hydrophilic monomer may be of the same kind of hydrophilic monomer (that is, the introduced hydrophilic spacer is the same), and may be a mixture of a plurality of hydrophilic monomers of different kinds (that is, a mixture of monomers incorporating different kinds of hydrophilic spacers).

The resin of the present invention has the degree of hydrophobicity on the resin surface (hereinafter sometimes referred to as solid phase surface) reduced by introduction of the hydrophilic spacer. Therefore, the non-specific adsorption of proteins and the like to the resin is highly suppressed. This effect renders the resin of the present invention to be suitably usable for the analysis of intermolecular specific interactions, the identification of target molecules for ligands, and the like. Accordingly, the resin of the present invention is useful as a carrier for affinity chromatography. In affinity chromatography, a molecule desired to have a target molecule identified or desired to have the specific interaction with a target molecule analyzed (hereinafter sometimes referred to as ligand) is immobilized to the resin of the present invention, that is, the carrier of the present invention. Note that as used herein, the terms ligand and target molecule are intended to mean a combination of members that exhibit a specific intermolecular interaction with each other, and their designations are variable depending on which member of the combination to immobilize as the ligand to the solid phase and leave the other member as the target molecule, that is, which member to immobilize to the solid phase.

"A specific interaction" is a characteristic action to specifically recognize, and bind to, a particular ligand (a particular target molecule) only; the relation of a specific receptor to an agonist or antagonist, the relation of an enzyme to a substrate, and the relation of, for example, an FK506-binding protein (target molecule) to FK506 (ligand), of a steroid hormone receptor to a steroid hormone (e.g., dexamathason and glucocorticoid receptor), of HDAC to the anticancer agent Trapoxin, and the like apply to "a specific interaction". Meanwhile, "a non-specific interaction" refers to an action wherein the subjects of binding thereby encompass a broad range of molecules and are not limited to particular molecules, and which produces a situation that is variously changeable depending on reaction conditions; in the present invention, this term means an action with an unparticular molecule that binds or adsorbs to the ligand on a carrier or to the carrier surface. "A non-specific interaction" is risky in that the binding based on a "specific interaction" is possibly overlooked as it hampers, or is confused with, the binding of the ligand and the target molecule based on "a specific interaction".

In the present invention, "to analyze a specific interaction" is to obtain the extent of the specificity of the interaction between the ligand and the target molecule as interaction information, which can, for example, be obtained as numerical values of Kd, Ka and the like. In the present invention, "selection" means determining whether or not the molecule in question exhibits a specific interaction with the ligand on the basis of the above-described interaction information, and identifying the target molecule.

Immobilization of the ligand to the resin is based on the binding of the ligand and the hydrophilic spacer present on the resin surface. Depending on the ligand to be immobilized, it is also preferable that a linker to facilitate the binding with the hydrophilic spacer be introduced in advance. Whether or not the ligand has been immobilized to the carrier can be confirmed by utilizing a color developing reaction based on a particular structure or substituent and the like contained in the ligand or an optionally chosen group that has been bound and introduced to the ligand in advance, and the like. For example, the ninhydrin reaction, which recognizes amino groups, and the like can be utilized. The binding is performed by utilizing a reaction common performed in the art. As a convenient and accurate means, a method utilizing an amide bond formation reaction can be mentioned. This reaction can, for example, be performed according to "Peputido Gousei no Kiso to Jikken" (ISBN 4-621-02962-2, Maruzen, 1st edition issued in 1985). Regarding the reagents and solvents used in each reaction, those in common use in the art can be utilized, and are selected as appropriate depending on the binding reaction employed.

In the present invention, the ligand to be immobilized to the resin surface is not subject to limitation, and may be a known compound or a novel compound that will be developed in the future. Also, the ligand may be a low-molecular compound or a high-molecular compound. Here, a low-molecular compound refers to a compound having a molecular weight of less than about 1000; for example, organic compounds commonly usable as pharmaceuticals, derivatives thereof, and inorganic compounds can be mentioned; specifically, compounds produced by making use of a method of organic synthesis and the like, derivatives thereof, naturally occurring compounds, derivatives thereof, small nucleic acid molecules such as promoters, various metals, and the like can be mentioned; and desirably, organic compounds that can be used as pharmaceutical, derivatives thereof, and nucleic acid molecules can be used. Also, as the high-molecular compound, a compound having a molecular weight of about 1000 or more, which is a protein, a polynucleic acid, a polysaccharide, or a combination thereof, and the like can be mentioned, and a protein is desirable. These low-molecular compounds or high-molecular compounds are commercially available if they are known compounds, or can be obtained via steps such as collection, production and purification according to various publications. These may be of natural origin, or may be prepared by gene engineering, or may be is obtained by semi-synthesis and the like.

The resin of the present invention, as a solid phase carrier for affinity chromatography, can be used to select a target molecule on a ligand-immobilized solid phase carrier on the basis of the specific interaction with the ligand, and is useful (the solid phase carrier for affinity chromatography is hereinafter sometimes referred to as the solid phase carrier of the present invention). Therefore, the target molecule is not subject to limitation, as long as it specifically interacts with the ligand, and is expected to be a known compound in some cases or a novel substance in other cases. It does not matter whether the target molecule is a low-molecular compound or a high-molecular compound.

Analysis of the interaction of the ligand and the target molecule and selection of the target molecule are conveniently performed on the solid phase carrier of the present invention. When a candidate substance is anticipated as the target molecule, it is possible to bring the candidate substance alone into contact with the ligand on the solid phase carrier, measure the interaction therebetween, and determine whether or not the candidate substance is the target molecule for the ligand; usually, by bringing a sample that contains a plurality of substances (high-molecular compounds and/or low-molecular compounds) into contact with the ligand, and measuring the presence or absence of an interaction between each of the plurality of substances (the high-molecular compounds and/or the low-molecular compounds) and the ligand and the extent of the interaction, whether or not the candidate substance is the target molecule is determined and the molecule is selected. Here, the sample that contains a plurality of substances may consist essentially of known compounds, may contain some novel compounds, and may consist essentially of novel compounds. However, according to search of target molecules for ligands, or the recent advances in proteome analysis, it is desirable that the sample be a mixture essentially of compounds of known structures. As the sample consisting essentially of known compounds, a mixture of purified proteins prepared by gene engineering using *Escherichia coli* and the like, and the like can be mentioned; as the sample that contains some novel compounds, a cell or tissue extract (lysate) can be mentioned; as the sample that consists essentially of novel compounds, a mixture of novel proteins whose functions and structures are yet unknown, or newly synthesized compounds and the like, can be mentioned. When the sample is a mixture, especially when it contains known compounds, the contents of these compounds in the sample may optionally be set at desired levels in advance. From the viewpoint of search for ligand target molecule, the molecule to be selected is preferably a low-molecular compound or a high-molecular compound, and for the sake of search for a target molecule in the body of an animal such as a human, the molecule is preferably a high-molecular compound.

The solid phase carrier of the present invention can also be used to screen for a target molecule that exhibits a specific interaction with a ligand immobilized on the solid phase carrier, and is useful. The screening method specifically comprises at least the steps shown below.

(1) A Step for Bringing a Sample into Contact with the Solid Phase Carrier of the Present Invention The sample used in this step can comprise a plurality of substances as described above. The mode of embodiment thereof is not subject to limitation, and can be changed as appropriate depending on what principles, means and methods to use for contact with the solid phase carrier and the identification or analysis performed in the subsequent step (2). For example, when using a column packed with the resin (solid phase carrier) of the present invention, it is preferable that the sample be liquid. The method of bringing the sample into contact with the ligand-immobilized solid phase carrier of the present invention is not subject to limitation, as long as the ligand and the target molecule can bind together by a specific interaction on the ligand-immobilized solid phase carrier when the target molecule is present in the sample, and can be changed as appropriate depending on what principles, means and methods to use in the subsequent step (2). For example, when using a column packed with the ligand-immobilized resin of the present invention as the ligand-immobilized solid phase carrier, the contact can be conveniently performed by adding a liquefied sample to the column and passing the sample through the column (column method).

Also, for convenience, the contact can be performed by mixing the resin and the sample for a given time (batch method). The amount applied to the column, flow rate, eluting treatment, mixing time and the like are determined on the basis of conditions common employed for affinity chromatography.

(2) A Step for Identifying and Analyzing a Molecule that has Exhibited or has not Exhibited a Specific Interaction with the Ligand Although this step can be changed as appropriate depending on to the kind of ligand immobilized and the like, it is performed by various methods commonly used in the art to identify a low-molecular compound or a high-molecular compound. Also, the step will also be performable by a method that will be developed in the future. For example, when using a column packed with the ligand-immobilized resin of the present invention as the ligand-immobilized solid phase carrier, it is also possible to dissociate the target molecule bound to the ligand on the solid phase carrier from the ligand on the solid phase carrier by a treatment such as altering the polarity of the buffer solution or further adding the ligand in excess, and then identify the target molecule, or to extract the target molecule with a surfactant and the like while remaining in a state bound to the ligand on the solid phase, and then identify the target molecule. As the method of identification, specifically, known techniques such as electrophoresis, immunoblotting and immunoprecipitation, which employ immunological reactions, chromatography, mass spectrometry, amino acid sequencing, and NMR (especially for low-molecules), or combinations of these methods can be used. Although the step for identifying a molecule that does not bind to the ligand can also be conducted in accordance with the above-described method of identifying a molecule that binds to the ligand, it is preferable that a treatment such as concentration or crude purification be conducted in advance before entering the identification step, since molecules contained in the effluent from the column are the subjects of identification. On the basis of the data obtained and existing reports, each molecule is identified, and whether or not it is a target molecule is determined.

Also, this step may be automated. For example, it is also possible to directly read data on various molecules obtained by two-dimensional electrophoresis, and identify the molecules on the basis of existing databases.

By the same principle as the above-described screening method, the target molecule in the sample can be measured. As used herein, "measurement" encompasses various operations such as determining the presence or absence of the target molecule in the sample and the amount of the target molecule if present, changes in a property thereof, and the like. Such a measurement makes it possible to diagnose a disease considered to be mediated by the target molecule or ligand. As examples of the diagnosis, cancer marker detection and the like can be mentioned. Using the method of the present invention, a particular protein (target molecule in the sample) is concentrated, resulting in a reduction in noise, so that more accurate detection of a trace amount of target molecule is possible. The present invention encompasses optionally chosen uses of a resin prepared by polymerizing a monomer incorporating a hydrophilic spacer.

EXAMPLES

The present invention is hereinafter described in more detail by means of the following production examples and experimental examples, which examples, however, are not to be construed as limiting the scope of the present invention. Also, the individual compounds, reagents and the like used are commercially available or can be prepared on the basis of published reports and the like unless otherwise stated.

Crosslinking agent concentrations in these Production Examples are calculated using the equation shown below.

Crosslinking agent concentration(%)=molar number of the crosslinking agent/molar number of the monomer×100

Production Example 1

Synthesis of 17-allyl-14-(tert-butyl-dimethyl-silanyloxy)-1-hydroxy-12-{2-[4-(7-(tert-butyl-dimethyl-silanyloxy-carbonyl)heptanoyl-oxy)-3-methoxy-cyclohexyl]-1-methyl-vinyl}-23,25-dimethoxy-13,19,21,27-tetramethyl-11,28-diox-4-aza-tricyclo[22.3.1.0$^{4,9}$]octacos-18-ene-2,3,10,16-tetraone

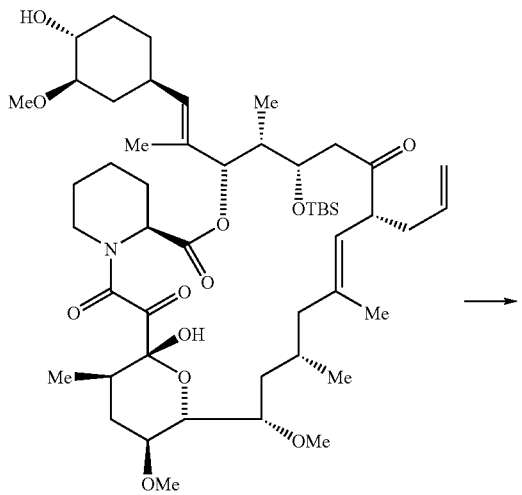

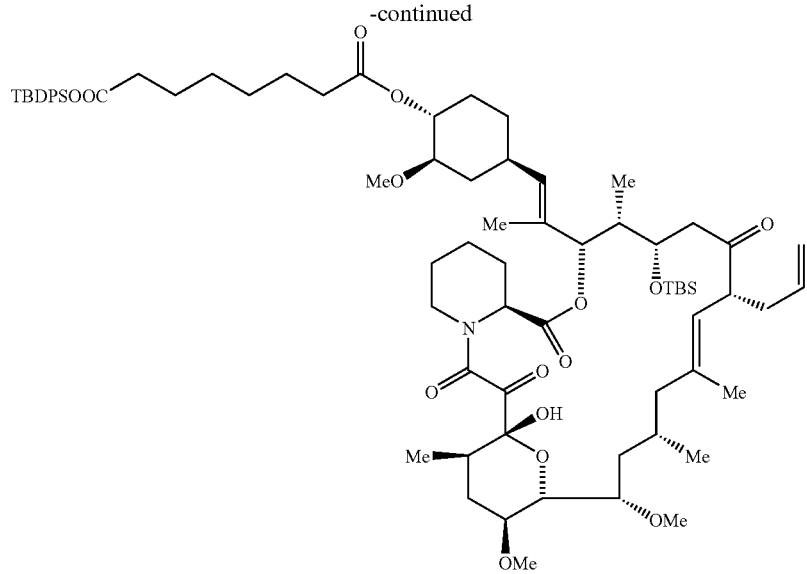

A mixture of 17-allyl-14-(tert-butyl-dimethyl-silanyloxy)-1-hydroxy-12-[2-(4-hydroxy-3-methoxy-cyclohexyl)-1-methyl-vinyl]-23,25-dimethoxy-13,19,21,27-tetramethyl-11,28-diox-4-aza-tricyclo[22.3.1.0$^{4,9}$]octacos-18-ene-2,3,10,16-tetraone (138 mg, 0.15 mmol), O-mono(tert-butyl-dimethyl-silanyl)octanedioic acid (86.7 mg, 0.218 mmol), dimethylaminopyridine (DMAP; 16.5 mg, 0.098 mmol), 1-[3-(dimethylamino)propyl]-3-ethylcarbodiimide hydrochloride (EDC/HCl; 69.1 mg, 0.261 mmol) and methylene chloride (CH$_2$Cl$_2$; 1 ml) was stirred at room temperature for 1.5 hours. The reaction product was poured over an ethyl acetate-water mixed liquid and extracted. The organic layer obtained was washed with water and saline, after which it was dried with magnesium sulfate (MgSO$_4$). After the MgSO$_4$ was separated by filtration, concentration under reduced pressure was conducted. The residue thus obtained was purified using a silica gel column (eluted with 20% AcOEt (in n-hexane)) to yield the desired 17-allyl-14-(tert-butyl-dimethyl-silanyloxy)-1-hydroxy-12-(2-[4-(7-(tert-butyl-dimethyl-silanyloxy-carbonyl)heptanoyl-oxy)-3-methoxy-cyclohexyl]-1-methyl-vinyl)-23,25-dimethoxy-13,19,21,27-tetramethyl-11,28-diox-4-aza-tricyclo[22.3.1.0$^{4,9}$]octacos-18-ene-2,3,10,16-tetraone (44 mg, 24.6%).

$^1$H-NMR(CDCl$_3$)δ: −0.1-0.1(12H,m), 0.7-2.6(47H,m), 0.85 and 0.86(18H,s), 1.50(3H,s), 1.63(3H,s), 2.75(1H,m), 3.31(3H,s), 3.35(3H,s), 3.39(3H,s), 4.05(1H,m), 3.0-4.4 (6H), 4.5-5.8(9H,m).

Production Example 2

Synthesis of 17-allyl-1,14-dihydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-diox-4-aza-tricyclo[22.3.1.0$^{4,9}$]octacos-18-ene-2,3,10,16-tetraone

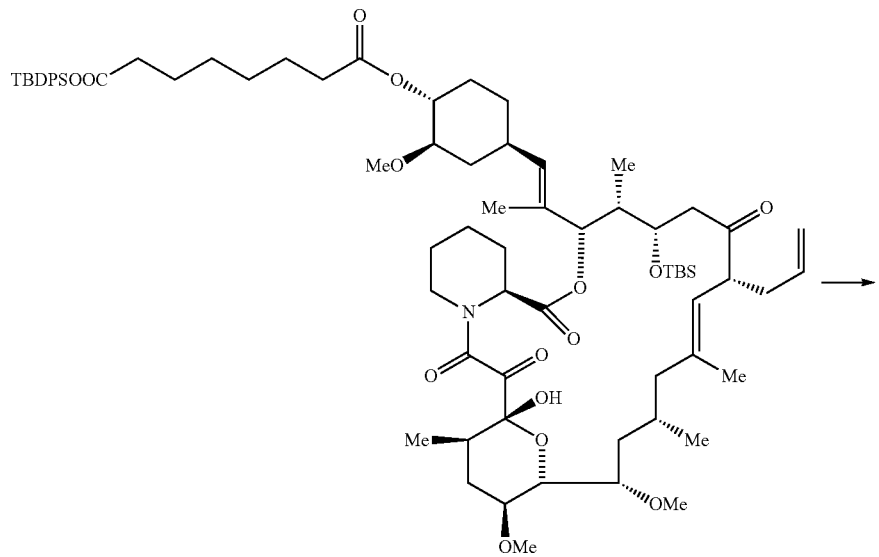

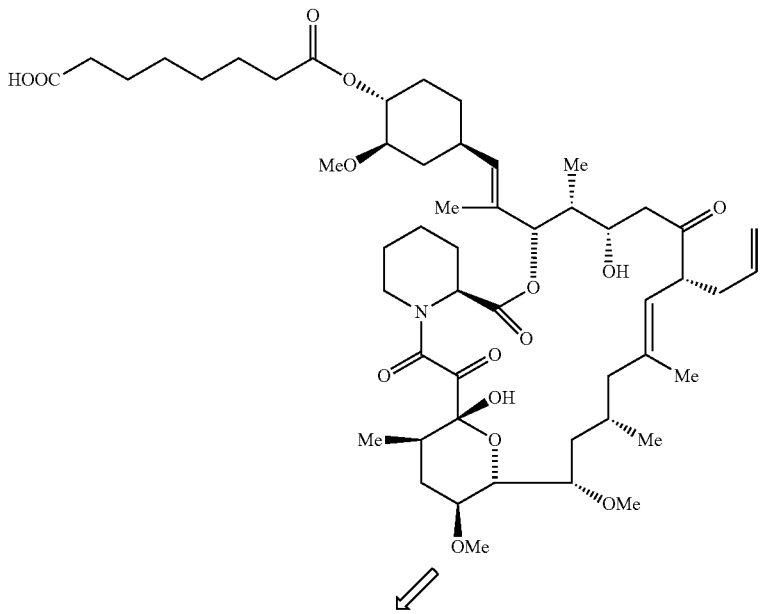

hereinafter abbreviated as:

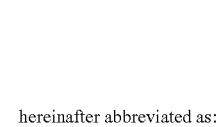

To a mixture of the 17-allyl-14-(tert-butyl-dimethyl-silanyloxy)-1-hydroxy-12-(2-[4-(7-(tert-butyl-dimethyl-silanyloxy-carbonyl)heptanoyl-oxy)-3-methoxy-cyclohexyl]-1-methyl-vinyl)-23,25-dimethoxy-13,19,21,27-tetramethyl-11,28-diox-4-aza-tricyclo[22.3.1.0$^{4,9}$]octacos-18-ene-2,3,10,16-tetraone prepared in Production Example 1 (44 mg, 0.037 mmol) and acetonitrile (0.88 ml), 46 to 48% aqueous hydrogen fluoride (HF) (0.12 ml) was gently added; this was followed by overnight stirring at room temperature. The reaction product was poured over an ethyl acetate-water mixed liquid and extracted. The organic phase obtained was washed with water and saline, after which it was dried with magnesium sulfate (MgSO$_4$). After the MgSO$_4$ was separated by filtration, concentration under reduced pressure was conducted. The residue thus obtained was purified using a silica gel column (5% methanol (in chloroform)) to yield the desired 17-allyl-1,14-dihydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-diox-4-aza-tricyclo[22.3.1.0$^{4,9}$]octacos-18-ene-2,3,10,16-tetraone (14.2 mg, 40%).

$^1$H-NMR(CDCl$_3$)δ: 0.7-2.6(47H,m), 1.50(3H,s), 1.63(3H, s), 2.75(1H,m), 3.31(3H,s), 3.35(3H,s), 3.39(3H,s), 4.05(1H, m), 3.0-4.4(6H), 4.5-5.8(11H,m).

MS(m/z): 960(M$^+$)

Production Example 3

Synthesis of TOYO-Pearl Resin (TSKgel AF-amino) with FK506

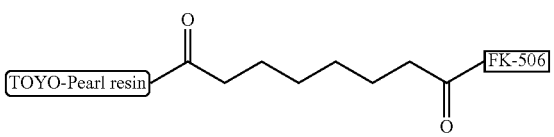

A mixture of the 17-allyl-1,14-dihydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-diox-4-aza-tricyclo[22.3.1.0$^{4,9}$]octacos-18-ene-2,3,10,16-tetraone prepared in Production Example 2 (38.4 mg, 0.04 mmol), TOYO-Pearl resin (TSKgel AF-amino, 100 μl, free amino group (available amino group) content 0.01 mmol), EDC/HCl (9.2 mg, 0.048 mmol), 1-hydroxybenzotriazole (HOBt; 6.5 mg, 0.048 mmol) and dimethylformamide (DMF; 1 ml) was stirred at room temperature for 6 hours. The reaction end point was confirmed as the time when no residual amino group became visually observable by the ninhydrin reaction. The reaction rate at this time was calculated to be about 82%. After confirmation of completion of the reaction, the resin was washed with DMF five times. Acetic anhydride (100 µl) and DMF (400 µl) were added thereto, and this was followed by stirring at room temperature for 1 hour. Subsequently, the resin was thoroughly washed with DMF, and the TOYO-Pearl resin with FK506 obtained was used in the binding experiments described below. The HBA number of the groups that interlie between the TOYO-Pearl resin and FK506 is 4 and the HBD number is 3 (however, those coming from the groups introduced to FK506 in advance are not counted).

Production Example 4

Synthesis of AffiGel Resin with FK506

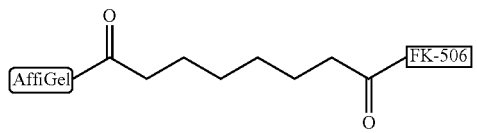

AffiGel resin with FK506 was synthesized by the same technique as Production Example 3 except that AffiGel resin (Bio-Rad Company) was used in place of TOYO-Pearl resin. The AffiGel resin with FK506 obtained was used in the binding experiments described below. The HBA number of the groups that interlie between the AffiGel resin and FK506 is 3 and the HBD number is 2 (however, those coming from the groups introduced to FK506 in advance are not counted).

Production Example 5

Synthesis of Hydrophilic Monomer: Synthesis of Methacrylic Acid 6-tert-butoxycarbonylamino-2,3,4,5-tetrahydroxyhexyl ester

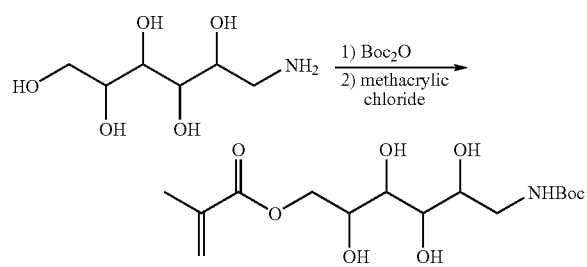

D-glucamine (5.0 g, 27.6 mmol) was dissolved by the addition of water (100 ml) and dioxane (100 ml). Next, di-tert-butyl dicarbonate (Boc$_2$O) (7.23 ml, 33.1 mmol) was added under ice cooling, after which the solution was stirred at room temperature overnight. The reaction liquid was concentrated and dissolved in methanol, and insoluble matter was filtered off, after which the filtrate was concentrated. The residue was dissolved in anhydrous pyridine (200 ml), and methacrylic chloride (3.74 ml, 38.6 mmol) was added drop by drop under ice cooling. After overnight stirring, the solution was concentrated, ethyl acetate was added to the residue, and the organic layer obtained was washed with a 2 N aqueous solution of potassium hydrogen sulfate, saturated aqueous sodium hydrogen carbonate, then with saturated saline, after which it was dried with sodium sulfate. After the solid was filtered off and the filtrate was concentrated under reduced pressure, the residue obtained was purified using a silica gel column (eluted with chloroform:methanol=100:7) to yield the desired methacrylic acid 6-tert-butoxycarbonylamino-2,3,4,5-tetrahydroxyhexyl ester (3.32 g, 34.4%).

$^1$H-NMR(DMSO-d$_6$)δ: 1.38(9H,s), 1.98(3H,s), 2.91-2.97 (1H,m), 3.10-3.16(1H,m), 3.45(1H,t), 3.57-3.61(2H,m), 3.72-3.77(1H,m), 4.04(1H,dd), 4.26-4.30(2H,m), 4.53(1H,d), 4.73(1H,d), 4.90(1H,d), 5.66(1H,t), 6.08(1H,s), 6.52(1H,t).

Production Example 6

Synthesis of Polyethylene Glycol (PEG) Type Hydrophilic Monomer: Synthesis of O-(2-methacryloylaminoethyl)-O-(2-tert-butoxycarbonylaminoethyl)hexaethylene glycol

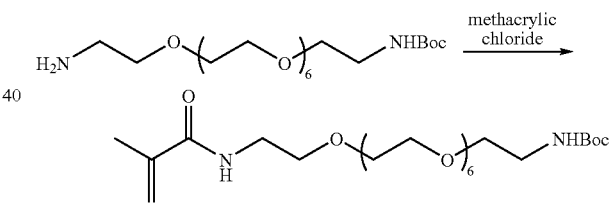

After dichloromethane (1.0 ml) and diisopropylamine (55.8 µl, 320 µmol) were added to O-(2-aminoethyl)-O-(2-tert-butoxycarbonylaminoethyl)hexaethylene glycol (100 mg, 213 µmol), methacrylic chloride (31.0 µl, 320 µmol) was added drop by drop under ice cooling. After the solution was stirred under ice cooling for 2 hours, ethyl acetate was added, the organic layer obtained was washed with a 2 N aqueous solution of potassium hydrogen sulfate, then with saturated saline, and dried with magnesium sulfate. After the solid was filtered off and the filtrate was concentrated under reduced pressure, the residue obtained was purified using a silica gel column (eluted with ethyl acetate:acetone=3:1) to yield the desired O-(2-methacryloylaminoethyl)-O-(2-tert-butoxycarbonylaminoethyl)hexaethylene glycol (69.3 mg, 61%).

$^1$H-NMR(CDCl$_3$)δ: 1.44(9H,s), 1.97(3H,s), 3.31-3.33 (2H,m), 3.50-3.55(4H,m), 3.57-3.69(26H,m), 5.06(1H,bs), 5.32(1H,t), 5.71(1H,s), 6.44(1H,bs).

MS(m/z): 537.4(MH$^+$)

Production Example 7

Synthesis of Hydrophilic Monomer (1) Synthesis of (2,3,4,5,6-pentahydroxy-hexyl)-carbamic acid 9H-fluoren-9-yl methyl ester (Fmoc-D-glucamine)

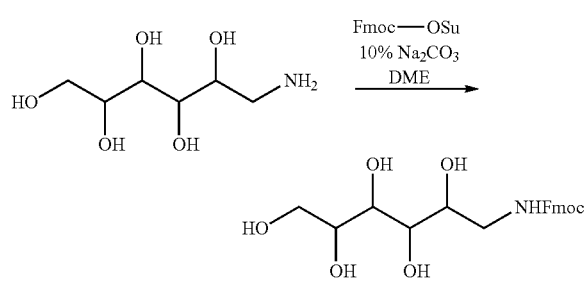

D-glucamine (9.0 g, 49.7 mmol) was mixed with 200 ml of a 10% aqueous solution of sodium carbonate, and this was followed by stirring under ice cooling. Fmoc-OSu (16.7 g, 49.7 mmol) was dissolved in 200 ml of DME and added to the reaction system, and this was followed by stirring under ice cooling for 30 minutes. The precipitating crystal was collected by filtration and washed with $H_2O \times 3$ and methanol ×3. The crystal was dried under reduced pressure to yield the desired F-moc body (2,3,4,5,6-pentahydroxy-hexyl)-carbamic acid 9H-fluoren-9-yl methyl ester (20 g) quantitatively.

$^1$H-NMR(DMSO-$d_6$)δ: 2.99-3.05(m,1H), 3.17-3.20(m,1H), 3.37-3.48(m,3H), 3.56-3.63(m,3H), 4.19-4.27(m,4H), 4.30-4.33(m,1H), 4.39-4.40(m,1H), 4.48-4.49(m,1H), 4.73(m,1H), 7.09-7.13(m,1H), 7.35(t,J=7.2 Hz,2H), 7.41(t,J=7.2 Hz,2H), 7.71(d,J=7.2H z), 7.88(d,J=7.2 Hz,2H).

MS(m/z): 404(MH$^+$).

(2) Synthesis of {6-[bis-(4-methoxy-phenyl)-phenyl-methoxy]-2,3,4,5-tetrahydroxy-hexyl}-carbamic acid 9H-fluoren-9-yl methyl ester

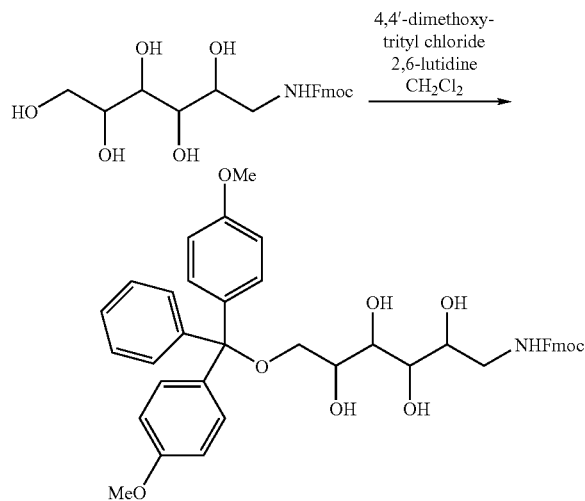

Fmoc-D-glucamine (5.0 g, 12.4 mmol) was dissolved in 100 ml of pyridine and azeotropically boiled. After this operation was conducted two times, the product was dissolved in 100 ml of dry pyridine and cooled with ice in a nitrogen stream. 4,4'-Dimethoxytrityl chloride (5.0 g, 14.9 mmol) and MAP (1.5 g, 12.4 mmol) were added, the temperature was gradually increased from under ice cooling to room temperature, and this was followed by stirring at room temperature for 17 hours. After the pyridine was distilled off under reduced pressure, the residue was diluted with 500 ml of ethyl acetate. After water was added, the organic layer was separated, after which the water layer was again extracted with ethyl acetate. The ethyl acetate layer was washed with saturated saline, after which it was dried with anhydrous magnesium sulfate. After concentration under reduced pressure, the concentrate was purified by silica gel column chromatography (CHCl$_3$:MeOH=10:1) to yield the desired compound (5.06 g) at a percent yield of 57.9%.

$^1$H-NMR(d-acetone)δ: 3.23-3.38(m,4H), 3.67-3.95(m,6H), 3.77(s,6H), 4.05(d,1H), 4.18-4.24(m,2H), 4.31-4.33(m,2H), 6.51(m,1H), 6.86(d,4H), 7.17-7.42(m,1H), 7.51(d,2H), 7.70(d,2H), 7.86(d,2H).

(3) Synthesis of [6-[bis-(4-methoxy-phenyl)-phenyl-methoxy]-2,3,4,5-tetrakis-(tert-butyl-dimethyl-silanyloxy)-hexyl]-carbamic acid 9H-fluoren-9-yl methyl ester

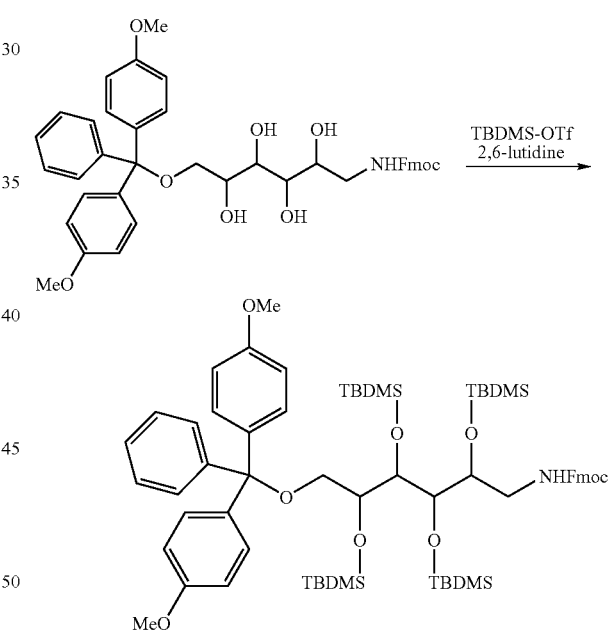

{6-[bis-(4-Methoxy-phenyl)-phenyl-methoxy]-2,3,4,5-tetrahydroxy-hexyl}-carbamic acid 9H-fluoren-9-yl methyl ester (2.46 g, 3.49 mmol) was dissolved in 2,6-lutidine (15 g, 140 mmol), and this was followed by stirring under ice cooling. TBDMS-OTf (18.4 g, 69.8 mmol) was gradually added. The temperature was returned from under ice cooling to room temperature, and this was followed by stirring for one day. 200 ml of dichloromethane and 200 ml of water were added, and this was followed by stirring at room temperature for 2 hours. After the organic layer was separated, the water layer was further extracted with 200 ml of dichloromethane. The dichloromethane layer was dried with anhydrous magnesium sulfate and concentrated under reduced pressure. The concentrate was purified by silica gel column chromatography (n-hexane:ethyl acetate=5:1) to yield the desired compound (3.5 g) at a percent yield of 86.4%.

$^1$H-NMR(CDCl$_3$)δ: −0.1-0.2(m,24H), 0.72(s,9H), 0.75(s,9H), 0.91-0.96(m,18H), 3.25(d,1H), 3.35-3.50(m,3H), 3.59 (m,1H), 3.75(s,6H), 3.80(m,1H), 4.03-4.19(m,3H), 4.29-4.41(m,2H), 5.18(m,1H), 6.76(d,J=8.4 Hz,4H), 7.15-7.21(m,9H), 7.27-7.34(m,4H), 7.47(t,J=7.2 Hz,2H), 7.65(d,J=7.2 Hz,2H).

(4) Synthesis of [2,3,4,5-tetrakis-(tert-butyl-dimethyl-silanyloxy)-6-hydroxyhexyl]-carbamic acid 9H-fluoren-9-yl methyl ester

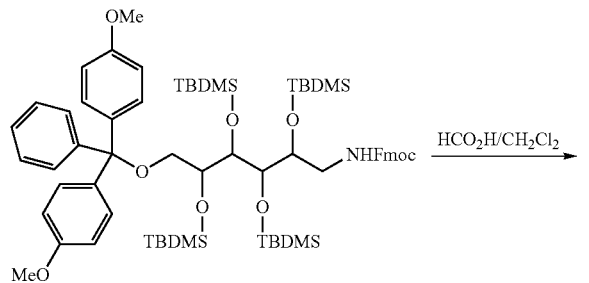

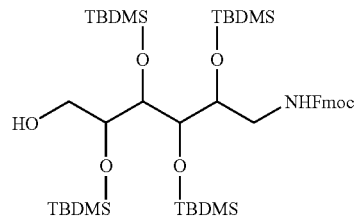

[6-[bis-(4-Methoxy-phenyl)-phenyl-methoxy]-2,3,4,5-tetrakis-(tert-butyl-dimethyl-silanyloxy)-hexyl]-carbamic acid 9H-fluoren-9-yl methyl ester (1.16 g, 1 mmol) was dissolved in 10 ml of a solution of formic acid:dichloromethane (1:10), and this was followed by stirring at room temperature for 2 hours. The reaction liquor was poured over saturated aqueous sodium bicarbonate and extracted with 100 ml of dichloromethane. The dichloromethane layer was dried with anhydrous magnesium sulfate and purified by silica gel column chromatography (n-hexane:ethyl acetate=10:1 to 5:1) to yield the desired alcohol body (600 mg) at a percent yield of 69.8%.

$^1$H-NMR(CDCl$_3$)δ: −0.50-0.10(m,24H), 0.77-0.87(m,36H), 2.10(m,1H) 3.29-3.36(m,1H), 3.43-3.56(m,2H), 3.57-3.61(m,1H), 3.65-3.71(m,1H), 3.75(m,1H), 4.03(m,1H), 4.09(m,1H), 4.27-4.32(m,2H), 4.90(m,1H), 7.17-7.21(m,2H), 7.29(t,J=7.6 Hz,2H), 7.49(t,J=7.6 Hz,2H), 7.66(d,J=7.6 Hz,2H).

MS(m/z): 860(MH$^+$).

(5) Synthesis of 2-methyl-acrylic acid 2,3,4,5-tetrakis-(tert-butyl-dimethyl-silanyloxy)-6-(9H-fluoren-9-yl methoxycarbonylamino)-hexyl ester

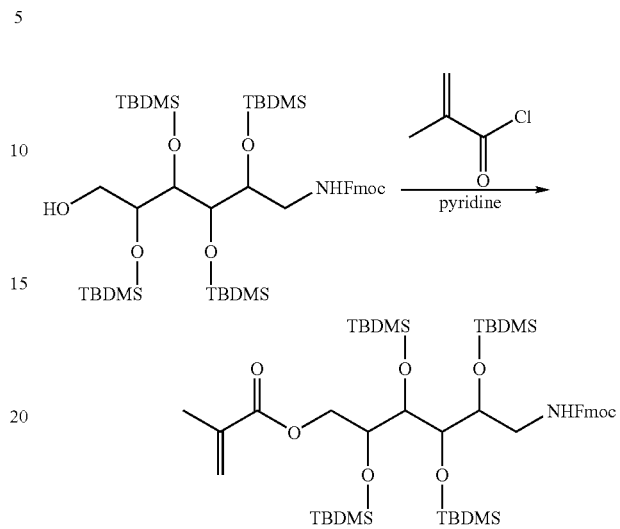

Dichloromethane (10 ml) was added to [2,3,4,5-tetrakis-(tert-butyl-dimethyl-silanyloxy)-6-hydroxyhexyl]-carbamic acid 9H-fluoren-9-yl methyl ester (460 mg, 0.54 mmol), and this was followed by stirring in a nitrogen stream at 5° C. Next, methacrylic chloride (560 mg, 5.4 mmol) was added drop by drop. The solution was stirred under ice cooling for 30 minutes, then stirred at room temperature for 30 minutes. Water was added to the reaction system, and extraction was twice performed with ethyl acetate. The organic layer obtained was washed with saturated saline, after which it was dried with sodium sulfate. After the solid was filtered off, the filtrate was concentrated under reduced pressure and purified by silica gel column chromatography to yield the desired 2-methyl-acrylic acid 2,3,4,5-tetrakis-(tert-butyl-dimethyl-silanyloxy)-6-(9H-fluoren-9-ylmethoxycarbonylamino)-hexyl ester (200 mg, 39%).

$^1$H-NMR(d-acetone)δ: 0.0-0.10(24H,m), 0.91(36H,m), 1.95(3H,s), 3.45(1H,m), 3.55(1H,m), 3.60(1H,m), 3.90-4.95 (7H,m), 5.00(1H,m), 5.55(1H,m), 6.10(1H,s), 7.29(2H,m), 7.39(2H,t), 7.58(2H,t), 7.75(2H,d).

Production Example 8

Synthesis of Resin A

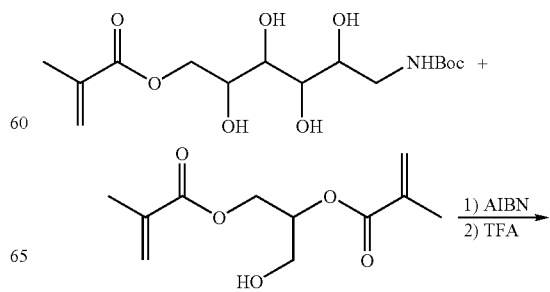

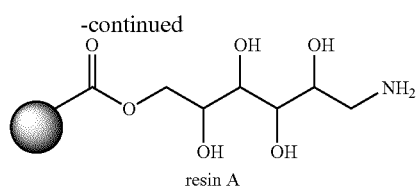
resin A 1,4-Dioxane (750 μl), glycerol dimethacrylate (3.50 μl, 17 μmol; crosslinking agent concentration about 2.0%) and azobisisobutyronitrile (AIBN: 1.65 mg) were added to the methacrylic acid 6-tert-butoxycarbonylamino-2,3,4,5-tetrahydroxyhexyl ester prepared in Production Example 5 (300 mg, 859 μmol), and the reaction was carried out in a nitrogen stream at 100° C. for 2 hours. The insoluble matter obtained was thoroughly washed with dimethylformamide (DMF), methanol, and diethyl ether, after which it was dried under reduced pressure. Forty milliliters (40 ml) of a mixed solution of trifluoroacetic acid, dichloromethane and 1,4-dioxane (2:1:1) was added to 200 mg of the 257 mg of resin obtained (84.6%); this was followed by stirring at room temperature for 1 hour. After completion of the reaction, the resin was thoroughly washed with 1,4-dioxane, methanol, diethyl ether, and DMF, after which it was stirred in a 5% solution of diisopropylethylamine/N-methyl-2-pyrrolidone (NMP) at room temperature overnight. Next, the resin was thoroughly washed with NMP, methanol, diethyl ether, DMF, and methanol, after which it was dried under reduced pressure to yield the desired resin A (141 mg). Note that the presence of about 4.9 μmol/mg amino groups in the resin was confirmed by the ninhydrin reaction.

Production Example 9

Synthesis of Resin A with FK506: Resin A-FK

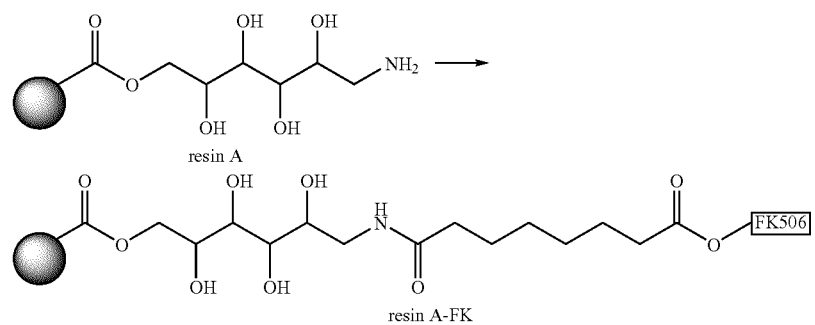

A mixture of the resin A prepared in Production Example 8 (20.0 mg, free amino group (available amino group) content 98 μmol), 17-allyl-1,14-dihydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-diox-4-aza-tricyclo[22.3.1.0$^{4,9}$]octacos-18-ene-2,3,10,16-tetraone (9.4 mg, 9.8 μmol), EDC/HCl (4.5 mg, 23 μmol), 1-hydroxybenzotriazole (HOBt; 3.2 mg, 24 μmol) and N-methyl-2-pyrrolidone (NMP; 0.5 ml) was stirred at room temperature overnight. The reaction end point was confirmed by HPLC as the time when the 17-allyl-1,14-dihydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-diox-4-aza-tricyclo[22.3.1.0$^{4,9}$]octacos-18-ene-2,3,10,16-tetraone nearly disappeared. The reaction rate at this time was calculated to be about 9%. After confirmation of completion of the reaction, the resin was thoroughly washed with DMF, methanol, diethyl ether, and DMF:H$_2$O (1:1). Acetic anhydride:DMF (1:9) (1.5 ml) was added thereto, and this was followed by stirring at room temperature for 1 hour. After washing with methanol, the reaction was confirmed by the ninhydrin reaction, and the reaction using a mixed solution of acetic anhydride and DMF (1:9) was repeated until no residual amino groups became visually observable. After confirmation of completion of the reaction, the resin was thoroughly washed with DMF, methanol, and diethyl ether, after which the resin A with FK506 (resin A-FK) obtained was used in the binding experiments described below.

Production Example 10

Synthesis of Resin B by Copolymerization with Ethyl Methacrylate

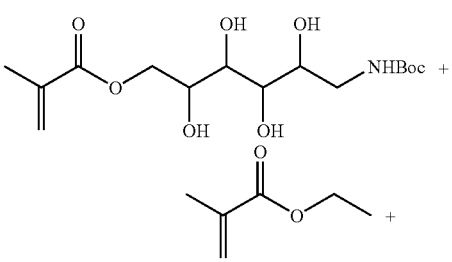

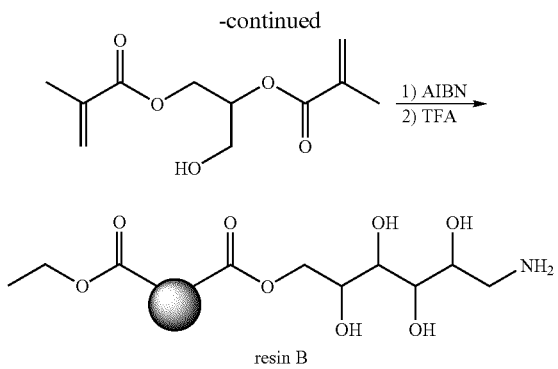
resin B 1,4-Dioxane (750 µl), ethyl methacrylate (96.2 µl, 773 µmol), glycerol dimethacrylate (20.6 µl, 86 µmol; crosslinking agent concentration about 10.0%) and azobisisobutyronitrile (AIBN: 1.4 mg) were added to the methacrylic acid 6-tert-butoxycarbonylamino-2,3,4,5-tetrahydroxyhexyl ester prepared in Production Example 5 (30 mg, 86 µmol); the reaction was carried out, in a nitrogen stream at 100° C. for 24 hours. The insoluble matter obtained was thoroughly washed with dimethylformamide (DMF), methanol, and diethyl ether, after which it was dried under reduced pressure. Eight milliliters (8 ml) of a mixed solution of trifluoroacetic acid and dichloromethane (1:1) was added to the 101 mg of resin obtained (72%); this was followed by stirring at room temperature for 1 hour. After completion of the reaction, the resin was thoroughly washed with DMF, after which it was stirred in a 5% solution of diisopropylethylamine/DMF at room temperature overnight. Next, the resin was thoroughly washed with DMF and diethyl ether, after which it was dried under reduced pressure to yield the desired copolymer (85 mg). Note that the presence of about 0.63 µmol/mg amino groups in the resin was confirmed by the ninhydrin reaction.

Production Example 11

Synthesis of Resin B with FK506: Resin B-FK

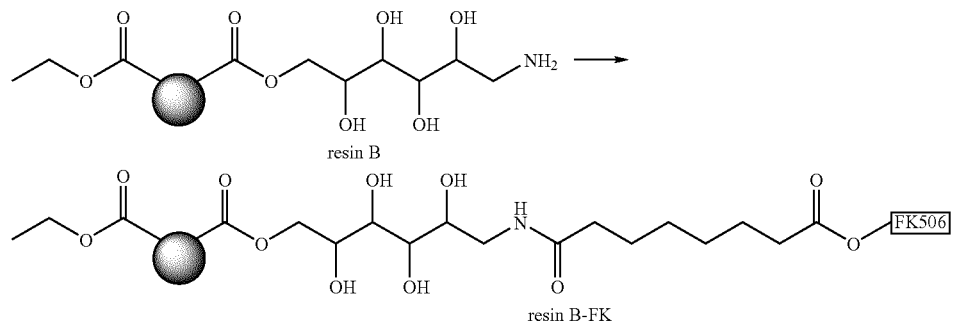

A mixture of the resin B prepared in Production Example 10 (16 mg, free amino group (available amino group) content 10 µmol), 17-allyl-1,14-dihydroxy-12-{2-[4-(7-carboxy-heptanoyl-oxy)-3-methoxy-cyclohexyl]-1-methyl-vinyl}-23,25-dimethoxy-13,19,21,27-tetramethyl-11,28-diox-4-aza-tricyclo[22.3.1.0$^{4,9}$]octacos-18-ene-2,3,10,16-tetraone (38.4 mg, 0.04 mmol), EDC/HCl (9.2 mg, 0.048 mmol), 1-hydroxybenzotriazole (HOBt; 6.5 mg, 0.048 mmol) and dimethylformamide (DMF; 0.5 ml) was stirred at room temperature-overnight. The reaction end point was confirmed as the time when no residual amino groups became visually observable by the ninhydrin reaction. The reaction rate at this time was calculated to be 100%. After confirmation of completion of the reaction, the resin was thoroughly washed with DMF, methanol, and diethyl ether. A mixed solution of acetic anhydride, methanol and N-methyl-2-pyrrolidone (NMP) (1:1:8) (1.0 ml) was added thereto, and this was followed by stirring at room temperature for 1 hour. Subsequently, the resin was thoroughly washed with DMF, methanol, and diethyl ether to yield resin B with FK506 (resin B-FK).

Production Example 12

Synthesis of Resin C by Copolymerization with Ethyl Methacrylate

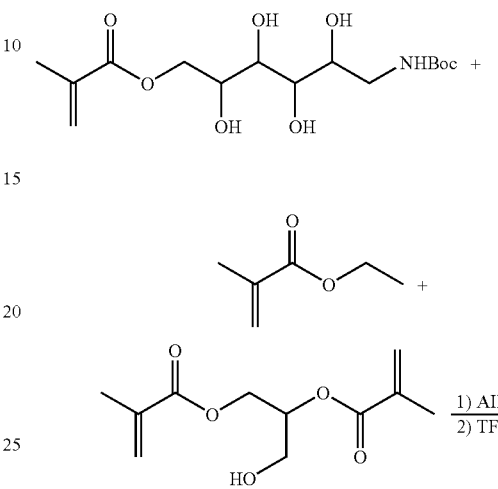

-continued

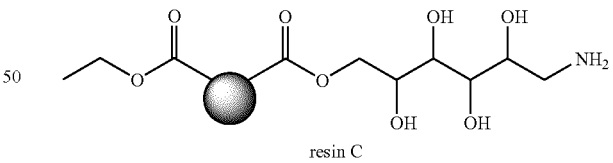

Resin C (141 mg) was obtained in the same manner as Production Example 8, using the methacrylic acid 6-tert-butoxycarbonylamino-2,3,4,5-tetrahydroxyhexyl ester prepared in Production Example 5 (90 mg, 258 µmol), ethyl methacrylate (289 µl, 2.32 mmol), glycerol dimethacrylate (10.5 µl, 43.8 µmol; crosslinking agent concentration about 1.7%), azobisisobutyronitrile (AIBN: 4.2 mg) and 1,4-dioxane (750 µl). Note that the presence of about 1.5 µmol/mg amino groups in the resin was confirmed by the ninhydrin reaction.

Production Example 13

Synthesis of Resin C with FK506: Resin C-FK

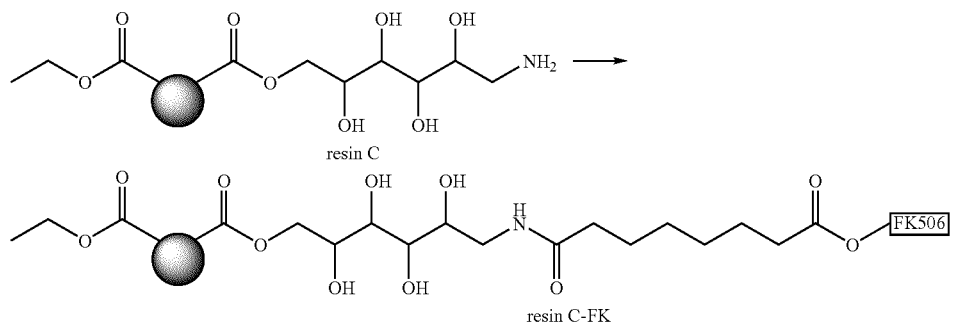

Resin C with FK506 (resin C-FK) was obtained from the resin C prepared in Production Example 12 (6.7 mg, free amino group (available amino group) content 10 μmol), in the same manner as Production Example 11.

Production Example 14

Synthesis of Resin D by Copolymerization with Ethyl Methacrylate

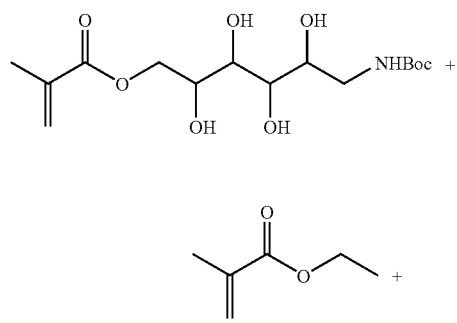

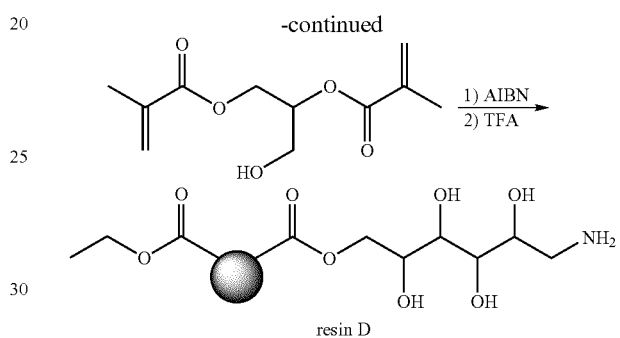

Resin D (117 mg) was obtained in the same manner as Production Example 8, using the methacrylic acid 6-tert-butoxycarbonylamino-2,3,4,5-tetrahydroxyhexyl ester prepared in Production Example 5 (150 mg, 429 μmol), ethyl methacrylate (441 μl, 3.86 mmol), glycerol dimethacrylate (17.5 μl, 73.0 μmol; crosslinking agent concentration about 1.7%), azobisisobutyronitrile (AIBN: 7.1 mg) and 1,4-dioxane (750 μl). Note that the presence of about 1.3 μmol/mg amino groups in the resin was confirmed by the ninhydrin reaction.

Production Example 15

Synthesis of Resin D with FK506: Resin D-FK

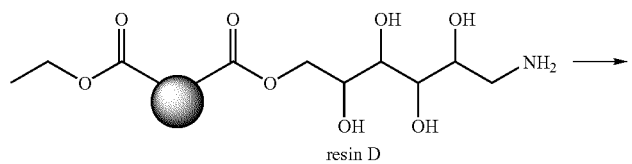

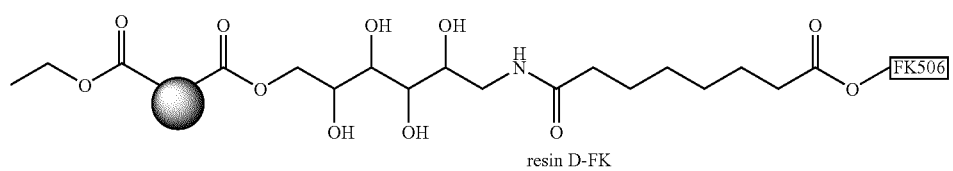

Resin D with FK506 (resin D-FK) was obtained from the resin D prepared in Production Example 14 (7.7 mg, free amino group (available amino group) content 10 μmol), in the same manner as Production Example 11.

Production Example 16

Synthesis of Resin E by Copolymerization with Methyl Methacrylate

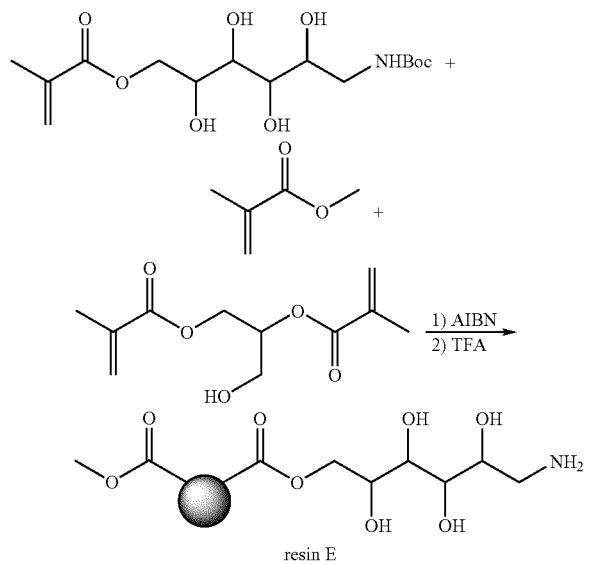

resin E

Resin E (59 mg) was obtained in the same manner as Production Example 8, using the methacrylic acid 6-tert-butoxycarbonylamino-2,3,4,5-tetrahydroxyhexyl ester prepared in Production Example 5 (30 mg, 85.9 μmol), methyl methacrylate (82.7 μl, 773 μmol), glycerol dimethacrylate (20.6 μl, 85.9 μmol; crosslinking agent concentration about 10%), azobisisobutyronitrile (AIBN: 1.4 mg) and 1,4-dioxane (750 μl). Note that the presence of about 0.89 μmol/mg amino groups in the resin was confirmed by the ninhydrin reaction.

Production Example 17

Synthesis of Resin E with FK506: Resin E-FK

Resin E with FK506 (resin E-FK) was obtained from the resin E prepared in Production Example 16 (11 mg, free amino group (available amino group) content 10 μmol), in the same manner as Production Example 11.

Production Example 18

Synthesis of Resin F by Copolymerization with Methyl Methacrylate

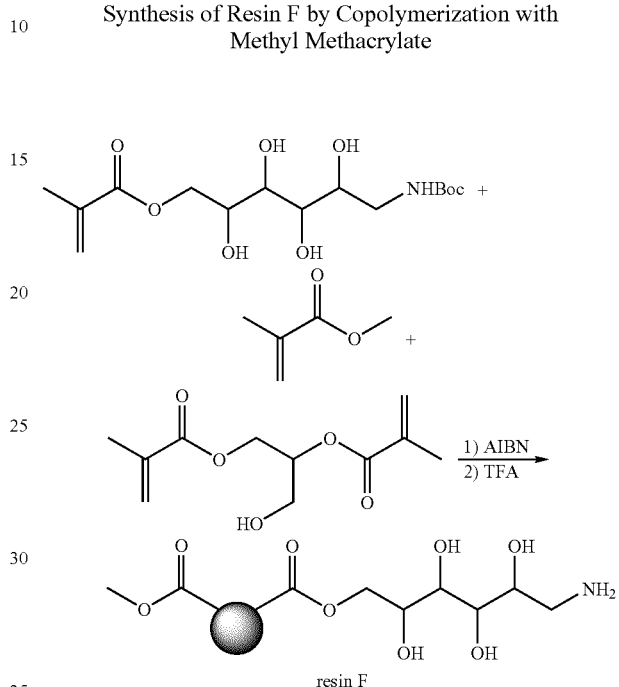

resin F

Resin F (171 mg) was obtained in the same manner as Production Example 8, using the methacrylic acid 6-tert-butoxycarbonylamino-2,3,4,5-tetrahydroxyhexyl ester prepared in Production Example 5 (90 mg, 258 μmol), methyl methacrylate (248 μl, 2.32 mmol), glycerol dimethacrylate (10.5 μl, 43.8 μmol; crosslinking agent concentration about 1.7%), azobisisobutyronitrile (AIBN: 4.2 mg) and 1,4-dioxane (750 μl). Note that the presence of about 0.84 μmol/mg amino groups in the resin was confirmed by the ninhydrin reaction.

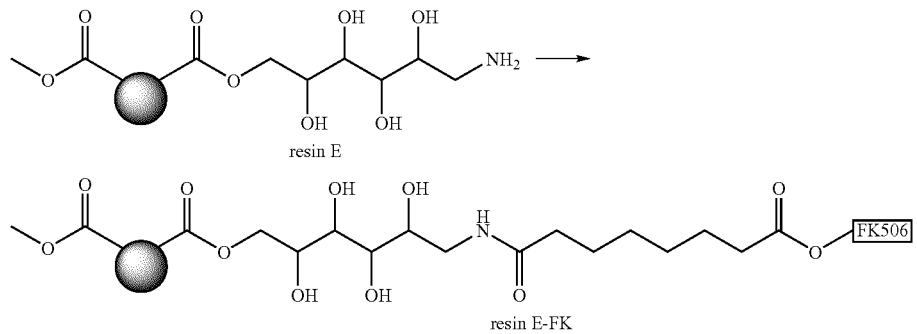

resin E resin E-FK

Production Example 19

Synthesis of Resin F with FK506: Resin F-FK

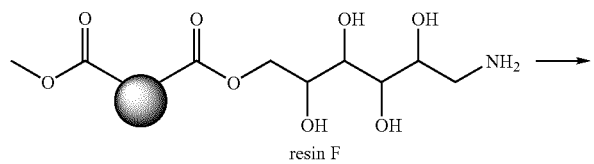

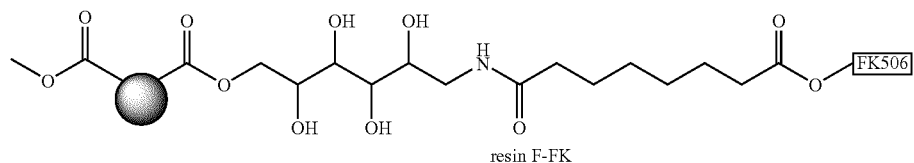

Resin F with FK506 (resin F-FK) was obtained from the resin F prepared in Production Example 18 (12 mg, free amino group (available amino group) content 10 mmol), in the same manner as Production Example 11.

Production Example 20

Synthesis of Resin G by Copolymerization with Methyl Methacrylate

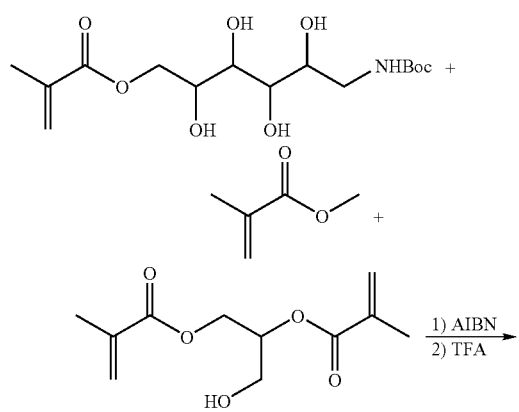

-continued

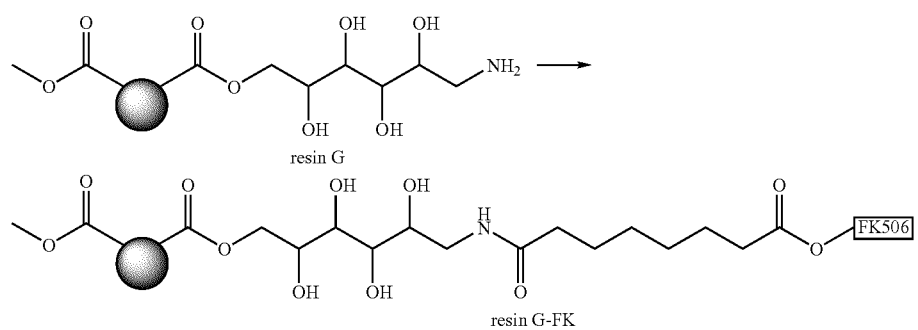

Resin G (243 mg) was obtained in the same manner as Production Example 8, using the methacrylic acid 6-tert-butoxycarbonylamino-2,3,4,5-tetrahydroxyhexyl ester prepared in Production Example 5 (150 mg, 429 μmol), methyl methacrylate (413 μl, 3.86 mmol), glycerol dimethacrylate (17.5 μl, 73.0 μmol; crosslinking agent concentration about 1.7%), azobisisobutyronitrile (AIBN: 7.1 mg) and 1,4-dioxane (750 μl). Note that the presence of about 1.5 μmol/mg amino groups in the resin was confirmed by the ninhydrin reaction.

Production Example 21

Synthesis of Resin G with FK506: Resin G-FK

Resin G with FK506 (resin G-FK) was obtained from the resin G prepared in Production Example 20 (6.5 mg, free amino group (available amino group) content 10 µmol), in the same manner as Production Example 11.

Production Example 22

Synthesis of Resin H by Copolymerization with Methacrylamide

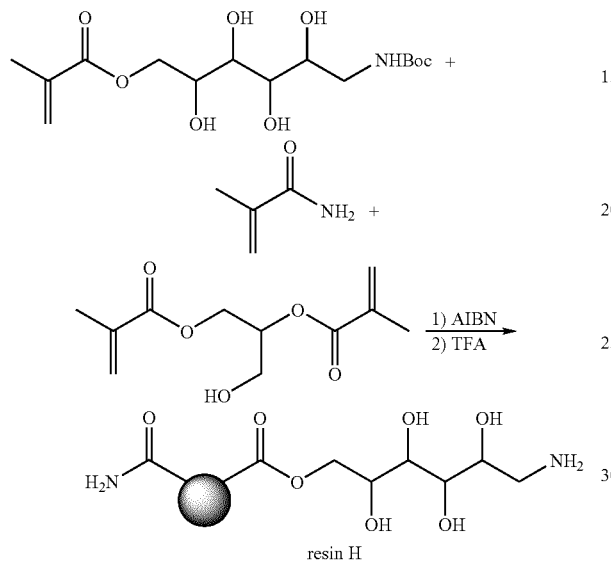

Resin H (9.7 mg) was obtained in the same manner as Production Example 8, using the methacrylic acid 6-tert-butoxycarbonylamino-2,3,4,5-tetrahydroxyhexyl ester prepared in Production Example 5 (30 mg, 85.9 µmol), methacrylamide (65.8 mg, 773 µmol), glycerol dimethacrylate (20.6 µl, 85.9 µmol; crosslinking agent concentration about 10.0%), azobisisobutyronitrile (AIBN: 1.4 mg) and 1,4-dioxane (750 µl). Note that the presence of about 0.72 µmol/mg amino groups in the resin was confirmed by the ninhydrin reaction.

Production Example 23

Synthesis of Resin H with FK506: Resin H-FK

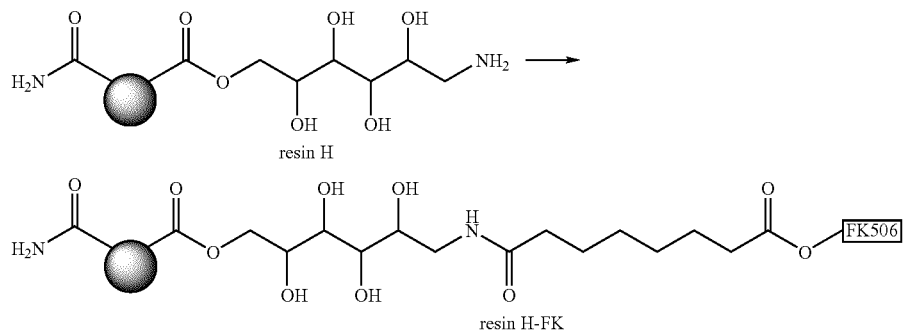

The desired resin H with FK506 (resin H-FK) was obtained from the resin H prepared in Production Example 22 (4.2 mg, free amino group (available amino group) content 3.0 µmol), in accordance with the method described in Production Example 11.

Production Example 24

Synthesis of Resin I by Copolymerization with Methacrylamide

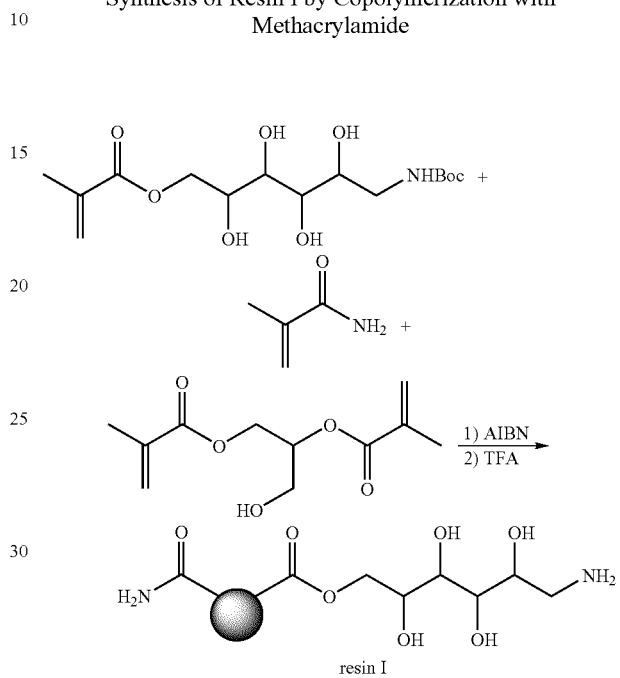

Resin I (99 mg) was obtained in the same manner as Production Example 8, using the methacrylic acid 6-tert-butoxycarbonylamino-2,3,4,5-tetrahydroxyhexyl ester prepared in Production Example 5 (90 mg, 258 µmol), methacrylamide (197 mg, 2.32 mmol), glycerol dimethacrylate (10.5 µl, 43.8 µmol; crosslinking agent concentration about 1.7%), azobisisobutyronitrile (AIBN: 4.2 mg) and 1,4-dioxane (750 µl). Note that the presence of about 0.79 µmol/mg amino groups in the resin was confirmed by the ninhydrin reaction.

Production Example 25

Synthesis of Resin I with FK506: Resin I-FK

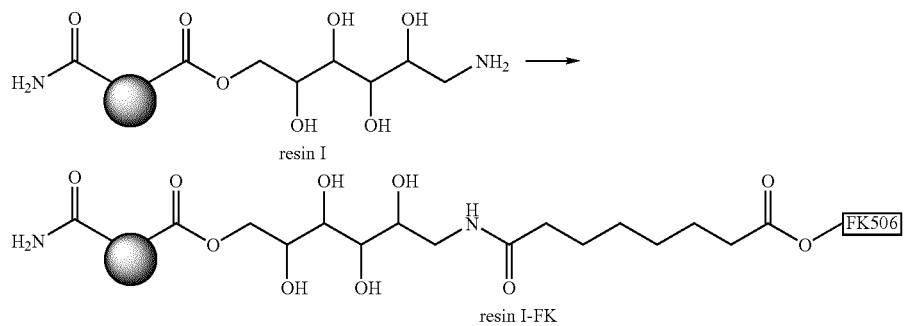

The desired resin I with FK506 (resin I-FK) was obtained from the resin I prepared in Production Example 24 (13 mg, free amino group (available amino group) content 10 μmol), in accordance with the method described in Production Example 11.

Production Example 26

Synthesis of Resin J by Copolymerization with Methacrylamide

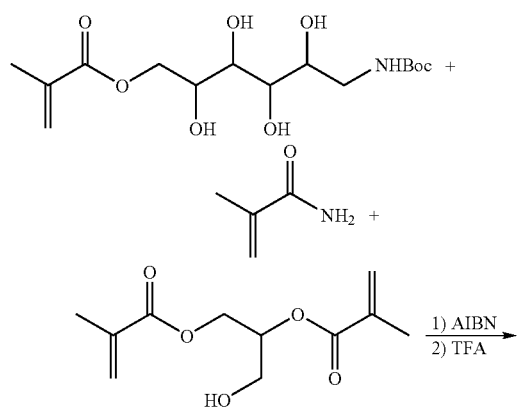

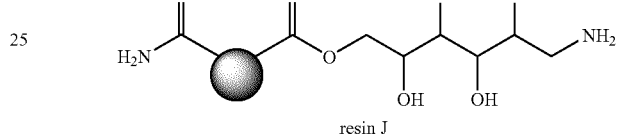

Resin J (62 mg) was obtained in the same manner as Production Example 8, using the methacrylic acid 6-tert-butoxycarbonylamino-2,3,4,5-tetrahydroxyhexyl ester prepared in Production Example 5 (150 mg, 429 μmol), methacrylamide (329 mg, 3.86 mmol), glycerol dimethacrylate (17.5 μl, 73.0 μmol; crosslinking agent concentration about 1.7%), azobisisobutyronitrile (AIBN: 7.1 mg) and 1,4-dioxane (750 μl). Note that the presence of about 1.2 μmol/mg amino groups in the resin was confirmed by the ninhydrin reaction.

Production Example 27

Synthesis of Resin J with FK506: Resin J-FK

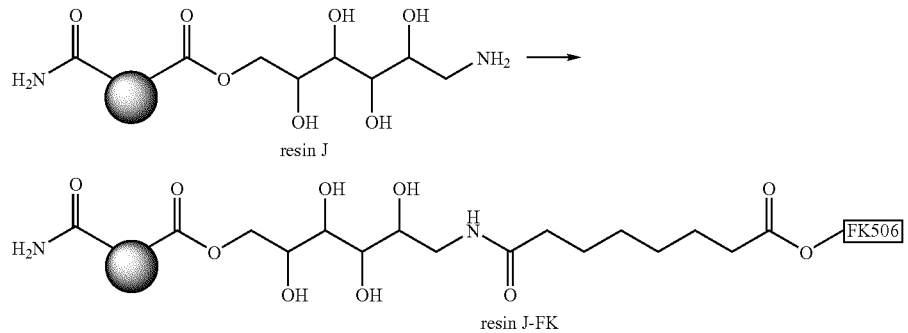

The desired resin J with FK506 (resin J-FK) was obtained from the resin J prepared in Production Example 26 (8.3 mg, free amino group (available amino group) content 10 μmol), in accordance with the method described in Production Example 11.

Production Example 28

Synthesis of PEG Type Hydrophilic Monomer (1) Synthesis of O-(2-phthalimidoethyl)pentaethylene glycol

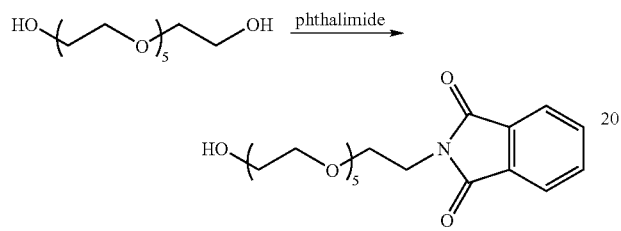

Tetrahydrofuran (600 ml), hexaethylene glycol (50 g, 177 mmol) and triphenylphosphine (55.7 g, 213 mmol) were added to phthalimide (31.3 g, 213 mmol). After diisopropylazodicarboxylate (40% toluene solution, 98.5 ml, 195 mmol) was added drop by drop under ice cooling, overnight stirring was performed at room temperature. The reaction liquid was concentrated, ethyl acetate was added to the residue, and the insoluble matter was filtered off. Saturated saline was added to the filtrate; after the filtrate was separated into two layers, the water layer was extracted with ethyl acetate, and the organic layers were combined. The organic layer obtained was dried with anhydrous sodium sulfate. After the solid was filtered off and the filtrate was concentrated under reduced pressure, the residue obtained was purified using a silica gel column (eluted with ethyl acetate:acetone=4:1) to yield the desired O-(2-phthalimidoethyl)pentaethylene glycol (32.7 g, 45%).

¹H-NMR(CDCl₃)δ: 3.58-3.69(18H,m), 3.71-3.75(4H,m), 3.90(2H,t), 7.71(2H,dd), 7.85(2H,dd).

MS(m/z): 412.2(MH⁺)

(2) Synthesis of O-(2-tert-butoxycarbonylaminoethyl)pentaethylene glycol

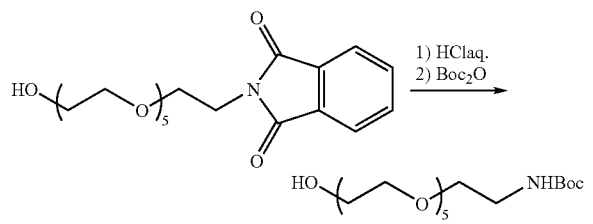

To the O-(2-phthalimidoethyl)pentaethylene glycol prepared in (1) above (8.13 g, 19.8 mmol), 8 N aqueous hydrochloric acid (25 ml) was added; this was followed by thermal refluxing for 5 hours. After cooling, the insoluble matter was filtered off, and the aqueous solution obtained was washed with chloroform and ethyl acetate. After dioxane (80 ml) was added to the water layer obtained, di-tert-butyl dicarbonate (5.19 g, 23.8 mmol) was added while adjusting to a pH 9 to 10 with an aqueous solution of sodium hydroxide. After stirring at room temperature for 1 hour, the reaction liquid was concentrated under reduced pressure to distill off the dioxane. The remaining aqueous solution was extracted with ethyl acetate, and the organic layers obtained were combined and dried with anhydrous sodium sulfate. After the solid was filtered off and the filtrate was concentrated under reduced pressure, the residue obtained was purified using a silica gel column (eluted with ethyl acetate:acetone=1:0 to 1:1) to yield the desired O-(2-tert-butoxycarbonylaminoethyl)pentaethylene glycol (4.66 g, 62%).

¹H-NMR(CDCl₃)δ: 1.44(9H,s), 3.32(2H,t), 3.54(2H,t), 3.60-3.69(18H,m), 3.73(2H,t), 5.22(1H,bs).

MS(m/z): 382.2(MH⁺)

(3) Synthesis of O-(2-tert-butoxycarbonylaminoethyl)-O-(2-methacryloyloxyethyl)tetraethylene glycol

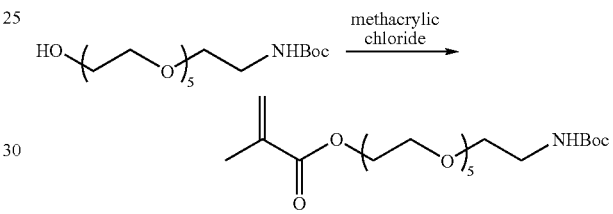

Diethyl ether (150 ml) was added to the O-(2-tert-butoxycarbonylaminoethyl)pentaethylene glycol prepared in (2) above (4.66 g, 12.2 mmol). Next, pyridine (3.7 ml) and methacrylic chloride (2.37 ml, 24.5 mmol) were added; this was followed by stirring for about 1 day. After hydroquinone (0.8 g) and ethyl acetate were added, the solution was sequentially washed with a saturated aqueous-solution of sodium hydrogen carbonate, a 2 N aqueous solution of citric acid, and saturated saline, after which the organic layer was dried with anhydrous sodium sulfate. After the solid was filtered off and the filtrate was concentrated under reduced pressure, the residue obtained was purified using a silica gel column (eluted with ethyl acetate) to yield the desired O-(2-tert-butoxycarbonylaminoethyl)-O-(2-methacryloyloxyethyl)tetraethylene glycol (4.46 g, 81%).

¹H-NMR(CDCl₃)δ: 1.44(9H,s), 1.95(1H,t), 3.30(2H,t), 3.54(2H,t), 3.60-3.68(16H,m), 3.75(2H,t), 4.30(2H,t), 5.06(1H,bs), 5.57(1H,t), 6.13(1H,bs).

MS(m/z): 467.3(MNa⁺)

Production Example 29

Synthesis of Resin K

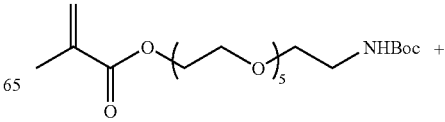

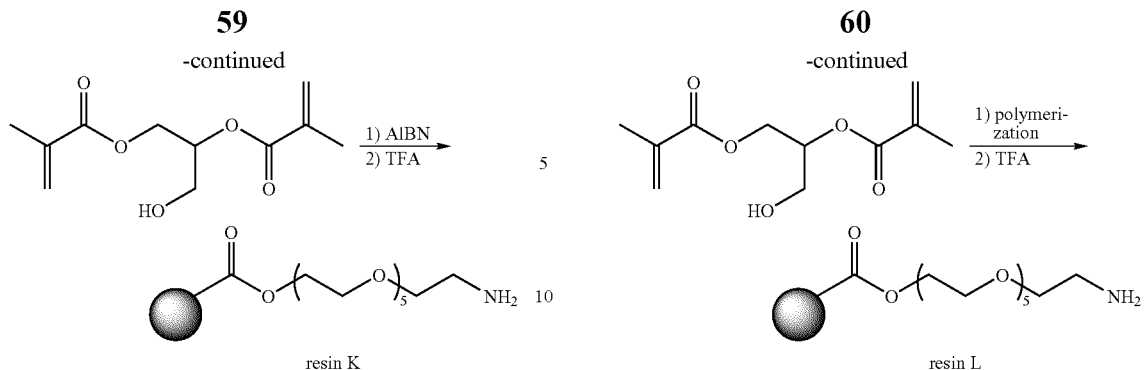

resin K            resin L

The desired resin K (122 mg) was obtained from the O-(2-tert-butoxycarbonylaminoethyl)-O-(2-methacryloyloxyethyl)tetraethylene glycol prepared in Production Example 28 (212 mg, 0.484 mmol), 1,4-dioxane (424 μl), glycerol dimethacrylate (11.6 μl, 0.048 mmol; crosslinking agent concentration 10%) and azobisisobutyronitrile (AIBN: 0.8 mg), in the same manner as Production Example 8. Note that the presence of about 3.8 μmol/mg amino groups in the resin was confirmed by the ninhydrin reaction.

Glycerol dimethacrylate (2.01 μl, 0.008 mmol; crosslinking agent concentration about 1.9%) and an aqueous solution of polyoxyethylene sorbitan monolaurate (54 mg)—ammonium persulfate (1 mg) (5.4 ml) were added to a butyl acetate solution (98 mg) of the O-(2-tert-butoxycarbonylaminoethyl)-O-(2-methacryloyloxyethyl)tetraethylene glycol prepared in Production Example 28 (188 mg, 0.418 mmol); this was followed by vigorous stirring to obtain an emulsified state. After overnight stirring at 70° C., the solution was thoroughly washed with water, DMF, and dioxane. Next, 40 ml of a mixed solution of trifluoroacetic acid and 1,4-dioxane (2:1) was added, and this was followed by overnight stirring at room temperature. After completion of the reaction, the resin was thoroughly washed with 1,4-dioxane and DMF, then further washed with an aqueous solution of sodium

Production Example 30

Synthesis of Resin K with FK506: Resin K-FK (Solution Polymerization)

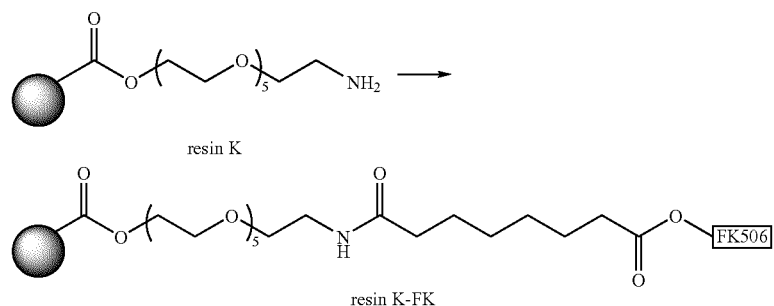

The desired resin K with FK506 (resin K-FK) was obtained from the resin K prepared in Production Example 29 (2.6 mg, free amino group (available amino group) content 3.8 μmol), in accordance with the method described in Production Example 11.

hydrogen carbonate, after which it was thoroughly washed with water and DMF to yield resin L.

Production Example 32

Synthesis of Resin M (Suspension Polymerization)

Production Example 31

Synthesis of Resin L (Emulsification Polymerization)

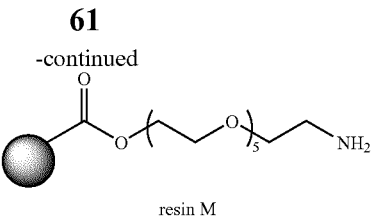

resin M

Glycerol dimethacrylate (2.01 µl, 0.008 mmol; crosslinking agent concentration about 1.9%), an aqueous solution of polyvinyl alcohol [1000, completely saponified type] (51 mg/2.6 ml), and calcium carbonate (14 mg) were added to a butyl acetate solution (98 mg) of the O-(2-tert-butoxycarbonylaminoethyl)-O-(2-methacryloyloxyethyl)tetraethylene glycol prepared in Production Example 28 (188 mg, 0.418 mmol). With vigorous stirring, the reaction was carried out at 70° C. for 1.5 hours and further at 80° C. for 1.5 hours. Next, the reaction product was thoroughly washed with water, DMF, and dioxane, after which 40 ml of a mixed solution of trifluoroacetic acid, dichloromethane and 1,4-dioxane (2:1:1) was added, and this was followed by stirring at room temperature for 1.5 hours. After completion of the reaction, the resin was thoroughly washed with 1,4-dioxane and DMF, after which it was stirred in a 5% solution of diisopropylethylamine/DMF at room temperature overnight. Next, the resin was thoroughly washed with DMF and methanol to yield resin M.

Production Example 33

Synthesis of Hydrophilic Monomer: Synthesis of Methacrylic Acid 6-(9H-fluoren-9-ylmethoxycarbonylamino)-2,3,4,5-tetrahydroxyhexyl ester

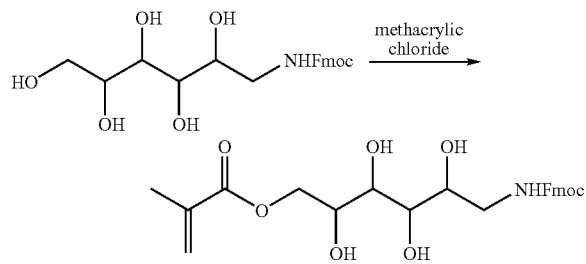

Anhydrous pyridine (300 ml) was added to the Fmoc-D-glucamine prepared in Production Example 7 (10 g, 24.9 mmol); methacrylic chloride (3.8 ml, 40.0 mmol) was added drop by drop under ice cooling, and this was followed by overnight stirring at room temperature. After methanol (100 ml) was added under ice cooling, the solution was concentrated. The residue was dissolved in ethyl acetate and washed with saturated saline, after which the organic layer was dried with magnesium sulfate. After the solid was filtered off and the filtrate was concentrated under reduced pressure, the residue obtained was purified using a silica gel column (eluted with chloroform:methanol=10:1) and crystallized from methanol-diethyl ether to yield the desired methacrylic acid 6-(9H-fluoren-9-ylmethoxycarbonylamino)-2,3,4,5-tetrahydroxyhexyl ester (2.29 g, 22.1%).

$^1$H-NMR(CDCl$_3$)δ: 1.95(3H,s), 3.16(1H,bs), 3.35-3.40 (3H,m), 3.68-3.72(3H,m), 3.82(1H,bs), 3.88(1H,m), 3.97(1H,m), 4.17(1H,t), 4.40(2 H,m), 5.37(1H,bs), 5.61(1H, s), 6.16(1H,s), 7.30(2H,t), 7.39(2H,t), 7.56(2H,d), 7.75(2H, d).

MS(m/z): 472.2(MH$^+$)

Production Example 34

Synthesis of Resin N (Emulsification Polymerization)

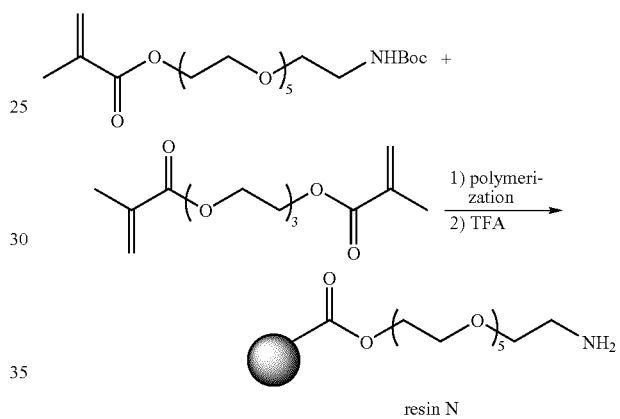

resin N

Butyl acetate (166 µl), triethylene glycol dimethacrylate (49.2 µl, 0.184 mmol; crosslinking agent concentration about 43%), and an aqueous solution of polyoxyethylene sorbitan monolaurate (79 mg/79 ml) were added to the O-(2-tert-butoxycarbonylaminoethyl)-O-(2-methacryloyloxyethyl) tetraethylene glycol prepared in Production Example 28 (193 mg, 0.429 mmol); this was followed by vigorous stirring to obtain an emulsified state. Ammonium persulfate (0.7 mg) was added, and this was followed by overnight stirring at 70° C., after which the solution was thoroughly washed with water, DMF, and dioxane. Next, 14 ml of a mixed solution of trifluoroacetic acid, 1,4-dioxane, dichloromethane and water (50:35:10:5) was added, and this was followed by overnight stirring at room temperature. After completion of the reaction, the resin was thoroughly washed with 1,4-dioxane and DMF, and further washed with a mixed liquid of an aqueous solution of sodium hydrogen carbonate and DMF, after which it was thoroughly washed with a water-DMF mixed solution and DMF to yield resin N. Note that the presence of about 0.350 mmol/ml amino groups in the resin was confirmed by the ninhydrin reaction.

Production Example 35

Synthesis of Resin N with FK506: Resin N-FK

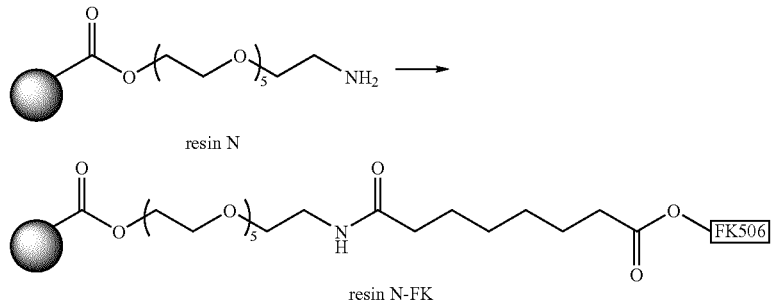

resin N-FK

The desired resin N with FK506 (resin N-FK) was obtained from the resin N prepared in Production Example 34 (a suspension equivalent to a free amino group content of 50 μmol), in accordance with the method described in Production Example 9 (resin A-FK).

Experimental Example 1

Binding Experiments (1) Preparation of Lysate

The rat brain (2.2 g) was mixed in a mixed liquid A (0.25 M sucrose, 25 mM Tris buffer (pH 7.4), 22 ml) and prepared as a homogenate, which was then centrifuged at 9000 rpm for 10 minutes. The centrifugal supernatant was collected and further centrifuged at 50000 rpm for 15 minutes. The supernatant thus obtained was used as the lysate. Note that all experiments were performed at 4° C. or on ice.

(2) Binding Experiments

Using the above-described various FK506-bound affinity resins, lysate binding experiments were performed per the procedures shown below. Note that the lysate was used after being diluted with the mixed liquid A at a dilution rate of 1/2. Ten microliters (10 μl) of each of the TOYO-Pearl resin with FK506 and AffiGel resin with FK506, a 0.1 μmol equivalent of resin A-FK, and a 1.0 μmol equivalent of each of resin B-FK to resin J-FK were used. Also, a 1.0 μmol equivalent of resin N-FK was used.

Each FK506-bound affinity resin and the lysate (1 ml) were gently shaken at 4° C. overnight. Thereafter, the supernatant was removed, and the remaining FK506-bound affinity resin was thoroughly washed with the mixed liquid A four times to thoroughly clean the surface of the FK506-bound affinity resin.

Twenty microliters (20 μl) of a loading buffer for SDS (Nakalai cat. NO=30566-22, sample buffer solution for electrophoresis with 2-ME (2-mercaptoethanol) (2×) for SDS PAGE) was added to the FK506-bound affinity resin thus obtained; this was followed by heating at 25° C. for 10 minutes. The sample liquid thus obtained was separated using a commercially available SDS gel (BioRad readyGel J, 15% SDS, cat. NO=161-J341), and the SDS gel was analyzed. The analysis was performed using SCANNER JX330 (SHARP) and ImageMaster version 2.01 (Pharmacia Biotech); out of the molecules that had bound (adsorbed) to the TOYO-Pearl resin with FK506 of Production Example 3, which is a Comparative Example, four representative bands (band 1 to band 4), including FKBP12 (band 4), were selected, and the amounts of the peaks thereof were measured for the resins of the Production Examples and Comparative Example, and quantified relative to the value for band 4 as the reference value (1.0) (the results for resin A-FK to resin J-FK are shown in FIG. 1). Separately conducted Western blotting confirmed the band 4 as FKBP12, that is, the target molecule for FK506.

The three remaining bands other than FKBP12 correspond to tubulin (band 1), actin (band 2), glyceraldehyde triphosphate dehydrogenase (band 3), respectively, and are non-specifically bound (adsorbed) to the TOYO-Pearl resin with FK506. For the resin A-FK to resin J-FK, as shown in FIG. 1, the non-specific binding (adsorption) of any protein to the solid phase surface was remarkably suppressed by using the resin of the present invention, and the non-specific adsorption was reduced to about the same extent as that obtained using the AffiGel resin with FK506. For the resin N-FK as well, the non-specific adsorption was remarkably suppressed.

The resin of the present invention, which is prepared by polymerizing a monomer component incorporating a hydrophilic spacer, and a ligand-immobilized solid phase carrier obtained by immobilizing a ligand to the resin, are capable of reducing the non-specific adsorption of substances, other than the target molecule for the ligand, which mingle in the sample, to the resin and/or the ligand. Therefore, target molecule search, identification and the like with less noise are enabled.

Preferred embodiments of this invention are described herein, including the best mode known to the inventors for carrying out the invention. It should be understood that the illustrated embodiments are exemplary only, and should not be taken as limiting the scope of the invention. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

The invention claimed is:

1. An affinity resin comprising a copolymer of a compound represented by the formula:

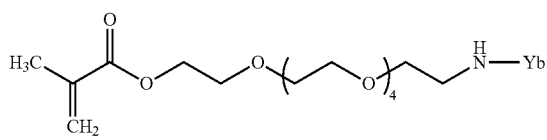

with a crosslinking agent wherein the crosslinking agent is selected from the group consisting of glycerol dimethylacrylate and triethylene glycol dimethylacrylate,
wherein Yb is a hydrogen atom or an amino-group-protecting group.

2. A screening method for a target molecule, which interacts specifically with a ligand, which method comprises:
(i) immobilizing the ligand to the resin of claim 1,
(ii) contacting the ligand-immobilized resin obtained in (i), with a sample, which may or may not comprise the target molecule,
(iii) identifying and/or analyzing the molecule, which interacts specifically or does not interact specifically with the ligand, and
(iv) judging the molecule that interacts specifically with the ligand to be a target molecule.

3. A method of measuring a target molecule, which interacts specifically with a ligand in a sample, which method comprises:
(i) immobilizing the ligand to the resin of claim 1,
(ii) contacting the ligand-immobilized resin obtained in (i) with a sample,
(iii) measuring and/or analyzing the molecule, which interacts specifically or does not interact specifically with the ligand, and
(iv) measuring a target molecule, which interacts specifically with the ligand.

* * * * *